(12) United States Patent
Bedford et al.

(10) Patent No.: US 9,675,594 B2
(45) Date of Patent: Jun. 13, 2017

(54) ARYLPYRROLOPYRIDINE DERIVED COMPOUNDS AS LRRK2 INHIBITORS

(71) Applicants: H. Lundbeck A/S, Valby (DK); Vernalis (R&D) Ltd., Winnersh (GB)

(72) Inventors: Simon Timothy Bedford, Winnersh (GB); I-Jen Chen, Winnersh (GB); Yikang Wang, Winnersh (GB); Douglas Stewart Williamson, Winnersh (GB)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/288,255

(22) Filed: Oct. 7, 2016

(65) Prior Publication Data
US 2017/0020850 A1 Jan. 26, 2017

Related U.S. Application Data

(62) Division of application No. 14/777,805, filed as application No. PCT/EP2014/057482 on Apr. 14, 2014, now Pat. No. 9,499,542.

(30) Foreign Application Priority Data

Apr. 18, 2013 (DK) .................................. 2013 00231

(51) Int. Cl.
| | | |
|---|---|---|
| *C07D 401/02* | (2006.01) | |
| *C07D 401/14* | (2006.01) | |
| *A61K 31/437* | (2006.01) | |
| *A61K 31/4353* | (2006.01) | |
| *C07D 471/04* | (2006.01) | |
| *A61K 31/444* | (2006.01) | |
| *A61K 31/5377* | (2006.01) | |

(52) U.S. Cl.
CPC .......... *A61K 31/437* (2013.01); *A61K 31/444* (2013.01); *A61K 31/5377* (2013.01); *C07D 471/04* (2013.01)

(58) Field of Classification Search
CPC .............................. C07D 401/02; C07D 401/14
USPC .......................... 546/119, 121; 514/300, 303
See application file for complete search history.

(56) References Cited

U.S. PATENT DOCUMENTS

| | | |
|---|---|---|
| 2010/0010037 A1 | 1/2010 | Brough et al. |
| 2014/0315901 A1 | 10/2014 | Bedford et al. |

FOREIGN PATENT DOCUMENTS

| | | |
|---|---|---|
| CN | 101679347 | 3/2010 |
| WO | 2004/101565 | 11/2004 |
| WO | 2007/076423 | 7/2007 |
| WO | 2008/025947 | 3/2008 |
| WO | 2008/115719 | 9/2008 |
| WO | 2012/038743 | 3/2012 |
| WO | 2012/138896 | 10/2012 |

OTHER PUBLICATIONS

Deng, X. et al. (2012) "Leucine-rich Repeat Kinase 2 Inhibitors: A Patent Review (2006-2011)," Expert Opinion on Therapeutic Patents 22(12):1415-1426.
Iaroshenko, V.O. et al. (2011) "Synthesis of Hereoannulated 3-nitro- and 3-aminopyridines by Cyclocondensation of Electron-Rich Aminoheterocycles with 3-nitrochromone," 68(11):2532-2543.
Volches-Herrea, M. et al. (2012) "One-Pot, Three-Component Synthesis of 7-Azaindole Derivatives from N-Substituted 2-Amino-4-cyanopyrroles, Various Aldehydes, and Active Methylene Compounds," ACS Comb. Sci. 14(7):434-441.

*Primary Examiner* — Niloofar Rahmani
(74) *Attorney, Agent, or Firm* — Jeffrey I. Auerbach; AuerbachSchrot LLC

(57) ABSTRACT

The present invention is directed to arylpyrrolopyridine derivatives of Formula A:

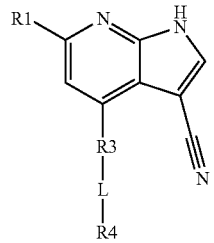

Formula A

The compounds are considered useful for the treatment of diseases associated with LRRK2 such as Lewy body dementia, Parkinson's disease or cancer.

12 Claims, No Drawings

ARYLPYRROLOPYRIDINE DERIVED COMPOUNDS AS LRRK2 INHIBITORS

CROSS-REFERENCE TO RELATED APPLICATIONS

This application is a divisional application of, and claims priority to, U.S. patent application Ser. No. 14/777,805 (filed on Sep. 17, 2015; issued as U.S. Pat. No. 9,499,542 on Nov. 22, 2016), herein incorporated by reference, which application is a §371 application of US Patent Application PCT/EP2014/057482 (filed on Apr. 14, 2014; now expired).

FIELD OF THE INVENTION

The present invention relates to arylpyrrolopyridine derivatives which are LRRK2 inhibitors and thus useful in therapy and to pharmaceutical composition comprising said compounds.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

Parkinson's disease is a neurodegenerative disease. It is the second most common neurodegenerative disease after Alzheimer's disease and affects more than 1% of the population above the age of 65. Parkinson's disease is clinically characterised by resting tremor, bradykinesia and muscular rigidity. Pathologically, the disease is characterised by loss of dopaminergic neurons with the consequent decrease in dopamine levels in the brain and by aggregation of the protein α-synuclein in the dopaminergic neurons. These aggregations called Lewy-bodies are composed of insoluble α-synuclein phosphorylated at serine-129 and ubiquitin. Current Parkinson's disease therapeutic intervention strategies aim at increasing the dopamine levels in areas innervated by dopaminergic neurons in the brain. Levadopa is a precursor of dopamine, and it is therapeutically used to increase dopamine levels. Carbidopa is an inhibitor of the enzyme aromatic-L-amino-acid decarboxylase also known as DOPA decarboxylase, and it is often co-administered with levadopa to increase the fraction of levadopa which reaches the clinically relevant regions in the brain. Monoamine oxidase B inhibitors are administered to increase the levels of dopamine by blocking the metabolism of dopamine. As an alternative, dopamine agonists are administered to stimulate dopaminergic neurons, an effect similar to that obtained by increasing the dopamine levels. Although these therapies provide significant symptomatic benefit to the patient, they are also associated with adverse side effects and often become ineffective after prolonged treatment. Importantly, neither of the existing therapies addresses the underlying and disease causing problem, i.e. the progressive loss or inactivation of dopaminergic neurons.

Leucine-Rich Repeat Kinase 2 (LRRK2) is a 2527 amino acid protein involved in catalysing phosphorylation and GTP-GTD hydrolysis. The NCBI reference sequence for human LRKK2 mRNA is NM_198578.2. Evidence is mounting showing a relationship between LRRK2 and the pathogenesis of Parkinson's disease. It has been shown that LRRK2 phosphorylates α-synuclein at serine-129, and as discussed above this phosphorylated form constitutes a significant part of the Lewy-bodies [Biochem Biophys Res Comm., 387, 149-152, 2009]. Additionally, single nucleotide polymorphisms in functional domains of LRRK2 have been shown to cause familiar and sporadic Parkinson's disease. So far at least 6 pathogenic variants have been identified, i.e. Gly2019Ser, Ile2020Thr, Arg1441Cys, Arg1441Gly, Arg1441His and Tyr1699Cys [Parkinsonism Rel. Dis., 15, 466-467, 2009; Movement Dis., 25, 2340-2345, 2010; Neuron, 44, 601-607, 2004; and Lancet, 365, 412-415, 2005]. Importantly, the clinical features of Parkinson's disease associated with LRRK2 mutations cannot be distinguished from those featuring in idiopathic Parkinson's disease. This strongly suggests a common pathogenic mechanism and that LRKK2 activity is a rate-limiting factor in Parkinson's disease progression [FEBS Journal, 276, 6436-6444, 2009].

The most common pathogenic form of LRRK2-associated Parkinson's disease is found in carriers of the amino acid substitution Gly2019Ser in the kinase domain of the LRRK2 protein. Gly2019Ser Parkinson's disease is inherited in an autosomal dominant fashion suggesting a gain-of-function mutation of the LRRK2 protein. In support of this notion, biochemical studies have shown that both the glycine to serine substitution at amino acid position 2019 as well as isoleucine to threonine substitution at amino acid position 2020 in the kinase domain lead to an increased kinase activity of LRRK2 [Proc. Nat. Acad. Sci USA, 102, 16842-16847, 2005]. This suggests a causal involvement of overactive LRRK2 in the pathogenesis of familiar forms of Parkinson's disease. Thus, inhibitors of LRRK2, including e.g. the G2019S and I2020T mutations, could be used as disease modifying treatment in familiar Parkinson's disease.

In cellular and animal studies several phosphorylation sites in the LRRK2 protein have been identified. Most prominent, phosphorylation of LRRK2 at two conserved residues serine at amino acid position 910 and serine at amino acid position 935 in human LRRK2 located just amino terminal to the leucine-rich repeat domain mediates binding to 14-3-3 proteins. Phosphorylation at serine residues 910 and 935 were shown to be dependent on an active LRRK2 conformation and further, that LRRK2 kinase inhibitors can inhibit phosphorylation at these two sites [Biochem J., 430, 405-13, 2010; J. Neurochem., 120:37-45, 2012].

LRRK2 kinase inhibitors have been shown to concentration-dependently inhibit LRRK2-Ser910 and LRRK2-Ser935 phosphorylation in cellular models expressing LRRK2 and LRRK2-G2019S as well as human LRRK2-expressing lymphoblastoid cells from PD patients homozygous for the LRRK2 G2019S mutation. In addition, LRRK2 kinase inhibition dose-dependently inhibits LRRK2-Ser910 and LRRK2-Ser935 phosphorylation in mouse brain after in vivo administration of an LRRK2 inhibitor. [ACS Med. Chem. Lett. 3 (8), 658-662, 2012.].

Common single nucleotide polymorphisms of LRRK2 have also been associated with Parkinson's disease [Nat Genet. 2009 December; 41(12):1308-12] [Mov Disorder 27(6) 1823-1826 2012]. A recent genome wide association meta-analysis study where correction for G2019S carrier status was performed indicated that common LRRK2 variants with minor allele frequency (MAF) above 1% also are associated with an increased risk of Parkinson's disease [Lancet. 377, 641-649, 2011]. Further, investigations of common exonic polymorphic variants have highlighted several LRRK2 Parkinson's disease risk variants: in Caucasians the M1646T mutation, in the Asian population the A419V mutation and also the previously found G2385R mutation. Genome studies have also identified other LRRK2 Parkinson's disease risk variants such as N551K, R1398H, K1423K, R1441G, R1441H, R1441C, R1628P, S1647T, Y1699C, I2020T and Y2189 [Lancet Neurol. 10, 898-908, 2011]. This indicates that LRRK2 inhibitors also could be useful as disease-modifying treatment in Parkinson's disease patients carrying common genomic LRRK2 variants such as M1646T, G2385R and A419V, in particular, but also common and rare LRRK2 variants such as N551K, R1398H, K1423K, R1441G, R1441H, R1441C, R1628P, S1647T, Y1699C, I2020T and Y2189C.

It has recently been demonstrated that the LRRK2 autophosphorylation on S1292 occurs in vivo and that it can be inhibited by LRRK2 kinase inhibition. In addition, the S1292 phosphorylation is enhanced by several of the familial Parkinson Disease LRRK2 variants. The autophosphorylation therefore serves as a valuable LRRK2 kinase activity indicator because familial Parkinson Disease LRRK2 variants increase the levels of LRRK2 autophosphorylation on S1292. However, since the Parkinson Disease variants increase the autophosphorylation, it has further been suggested that the phosphorylation S1292 may be important for the abnormal effects of the kinase, and thus be an important risk factor for Parkinson's disease [Science Trans. Med, Vol. 4, 164, 1-12, 2012].

Indeed, as discussed above, as the clinical features of LRRK2 associated and idiopathic Parkinson's disease are very similar this also suggests that LRRK2 inhibitors could be useful for the treatment of sporadic PD.

As established above, LRRK2 inhibitors may be used in the treatment of Parkinson's disease and particular mention is made of Parkinson's disease associated with mutations in LRRK2, such as Gly2019Ser. Moreover, LRRK2 inhibitors are also expected to be useful in the treatment of other diseases which are associated with LRRK2. LRRK2 has been identified as a core component in Lewy bodies and is thus expected to be useful in the treatment of Lewy body dementia [Neuropathol. Appl. Neurobiol., 34, 272-283, 2008]. Expression of LRRK2 mRNA is highly enriched in brain, lungs, kidney, spleen and blood suggesting that functional impact of increased LRRK2 activity is likely to be most relevant in pathogenic and pathologic conditions associated with those regions. Support for that notion can be found in studies showing an increased risk of non-skin cancer in LRRK2 Gly2019Ser mutation carriers and especially for renal and lung cancer [Mov. Disorder, 25, 2536-2541, 2010]. Over-expression of LRRK2 by chromosomal amplification has also been identified in papillary renal and thyroid carcinomas. Also, genetic association of LRRK2 has been reported to diseases in where aberrant responses of the immune system are involved. This is the case for inflammatory bowel diseases such as Crohn's disease and ulcerative colitis as well as for leprosy [Nat Genet. 42, 1118-1125, 2010; Inflamm. Bowel. Dis. 16, 557-558, 2010; N Engl. J Med. 361, 2609-2618, 2009; Inflamm. Bowel. Dis- .doi: 10.1002/ibd.21651, 2011].

To the inventors' knowledge no one has developed arylpyrrolopyridine derived compounds as LRRK2 inhibitors.

SUMMARY OF THE INVENTION

The present inventors have surprisingly found certain arylpyrrolopyridine derivatives which are LRRK2 inhibitors. Accordingly, in one embodiment the invention provides a compound of Formula A, below:

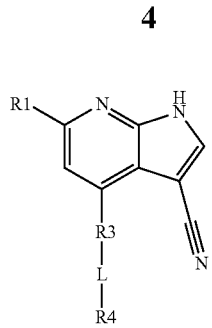

Formula A wherein
R1 represents H or a NHR2 group,
R2 represents H or a 5 or 6 membered heteroaromatic ring with 1 or 2 N, which heteroaromatic ring is optionally substituted with 1 or 2 groups each independently selected from the group comprising $CF_3$, halogen, $C_1$-$C_3$ alkyl, $C_1$-$C_3$ alkoxy, $C_1$-$C_3$ alkylamine or $C_1$-$C_3$ alkoxy amine,
R3 represents a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 $C_1$-$C_3$ alkyl, 1 or 2 $C_1$-$C_3$ alkoxy or a trifluoromethyl,
L is absent or represents $(CH_2)_n$, n=1 or 2,
R4 represents H, $NH_2$ or a 5 or 6 membered heterocylic ring with 1 or 2 heteroatom(s) selected from N or O, which heterocyclic ring is optionally substituted with 1 or 2 $C_1$-$C_3$ alkyl, 1 or 2 $C_2$-$C_3$ alkoxy, 1 or 2 $C_1$-$C_3$ alkyl amine or 1 or 2 $C_2$-$C_3$ alkoxy amine,
and pharmaceutical acceptable salts thereof,
with the proviso that the compound is not selected from
4-Phenyl-1H-pyrrolo[2,3-b]pyridine-3-carbonitrile,
4-(3-Hydroxyphenyl)-1H-pyrrolo[2,3-b]pyridine-3-carbonitrile or
4-(2,4-Dimethylphenyl)-1H-pyrrolo[2,3-b]pyridine-3-carbonitrile.

In one embodiment, the invention provides a pharmaceutical composition comprising a compound of the above formula A and pharmaceutically acceptable salts thereof together with a pharmaceutically acceptable excipient.

In one embodiment, the invention provides compounds of the above formula A and pharmaceutically acceptable salts thereof for use in therapy.

In one embodiment, the invention provides compounds of the above formula A and pharmaceutically acceptable salts thereof for use in a method for the treatment of a disease associated with LRRK2.

In one embodiment, the invention relates to the use of a compound of the above formula A and pharmaceutically acceptable salts thereof in the manufacture of a medicament for use in the treatment of a disease associated with LRRK2.

In one embodiment, the invention relates to a method for the treatment of a disease associated with LRRK2, the method comprising the administration of a therapeutically effective amount of a compound of the above formula A and pharmaceutically acceptable salts thereof to a patient in need thereof.

DETAILED DESCRIPTION OF THE INVENTION

According to an embodiment of the invention the compounds of formula A may have an R2 group selected from H or a 5 or 6 membered heteroaromatic ring with 1 or 2 N, which heteroaromatic ring is optionally substituted with 1 or 2 $C_1$-$C_3$ alkyl, 1 or 2 $C_1$-$C_3$ alkoxy, 1 or 2 $C_1$-$C_3$ alkylamine or 1 or 2 $C_1$-$C_3$ alkoxy amine.

According to another embodiment of the invention the compounds of formula A may have an R2 group selected from the following heteroaromatic rings

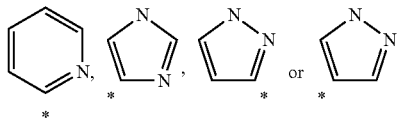

optionally substituted with 1 or 2 groups each independently selected from the group comprising $CF_3$, halogen, $C_1$-$C_3$ alkyl, $C_1$-$C_3$ alkoxy, $C_1$-$C_3$ alkylamine or $C_1$-$C_3$ alkoxy amine. * denotes the attachment point.

R3 may according to an embodiment be selected from the group comprising

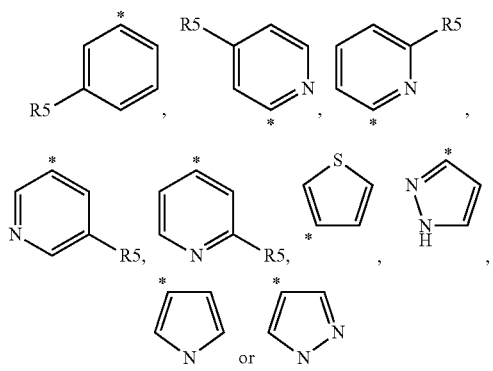

Furthermore, the compounds of formula A may in some embodiments have an —R3-L-R4 selected from the group comprising

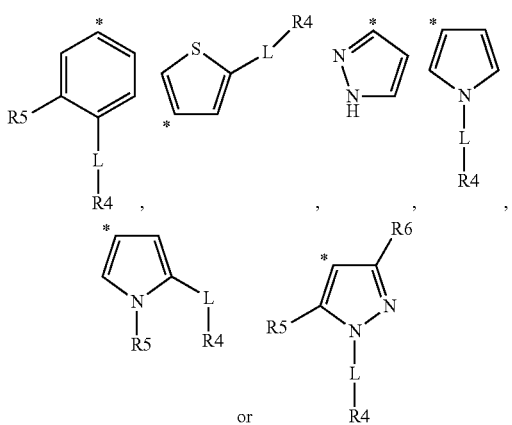

wherein R5 and R6 each independently represent H, $C_1$-$C_3$ alkyl or $C_1$-$C_3$ alkoxy and L and R4 are each independently defined herein above for formula A. * denotes the attachment point.

Furthermore, R4 may be represented by:

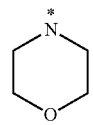

* denotes the attachment point.
In specific embodiments according to the invention the compounds are selected from
4-(3-Methoxyphenyl)-1H-pyrrolo[2,3-b]pyridine-3-carbonitrile,
4-(3-Methylphenyl)-1H-pyrrolo[2,3-b]pyridine-3-carbonitrile,
4-(3-Ethylphenyl)-1H-pyrrolo[2,3-b]pyridine-3-carbonitrile,
4-(Thiophen-3-yl)-1H-pyrrolo[2,3-b]pyridine-3-carbonitrile,
4-[4-(Morpholin-4-ylmethyl)phenyl]-1H-pyrrolo[2,3-b]pyridine-3-carbonitrile,
4-[1-(Morpholin-4-ylmethyl)pyrrol-3-yl]-1H-pyrrolo[2,3-b]pyridine-3-carbonitrile,
4-[3-Methyl-4-(morpholin-4-ylmethyl)phenyl]-1H-pyrrolo[2,3-b]pyridine-3-carbonitrile,
4-{4-[(Dimethylamino)methyl]-3-methylphenyl}-1H-pyrrolo[2,3-b]pyridine-3-carbonitrile,
4-[3-Ethyl-4-(morpholin-4-ylmethyl)phenyl]-1H-pyrrolo[2,3-b]pyridine-3-carbonitrile,
4-[3-Methoxy-4-(morpholin-4-ylmethyl)phenyl]-1H-pyrrolo[2,3-b]pyridine-3-carbonitrile,
6-Amino-4-phenyl-1H-pyrrolo[2,3-b]pyridine-3-carbonitrile,
6-Amino-4-(3-methylphenyl)-1H-pyrrolo[2,3-b]pyridine-3-carbonitrile,
6-[(1-Methylpyrazol-3-yl)amino]-4-phenyl-1H-pyrrolo[2,3-b]pyridine-3-carbonitrile,
4-(3-Methylphenyl)-6-[(1-methylpyrazol-3-yl)amino]-1H-pyrrolo[2,3-b]pyridine-3-carbonitrile,
4-[3-Methyl-4-(morpholin-4-ylmethyl)phenyl]-6-[(1-methylpyrazol-3-yl)amino]-1H-pyrrolo[2,3-b]pyridine-3-carbonitrile,
6-[(1-Methylpyrazol-4-yl)amino]-4-phenyl-1H-pyrrolo[2,3-b]pyridine-3-carbonitrile,
4-Phenyl-6-(pyridin-2-ylamino)-1H-pyrrolo[2,3-b]pyridine-3-carbonitrile,
6-{[1-Methyl-4-(trifluoromethyl)-1H-pyrazol-3-yl]amino}-4-(5-methylpyridin-3-yl)-1H-pyrrolo[2,3-b]pyridine-3-carbonitrile,
6-[(4-Chloro-1-methyl-1H-pyrazol-3-yl)amino]-4-(4-methylpyridin-2-yl)-1H-pyrrolo[2,3-b]pyridine-3-carbonitrile,
6-[(1,4-Dimethyl-1H-pyrazol-3-yl)amino]-4-(6-methylpyridin-2-yl)-1H-pyrrolo[2,3-b]pyridine-3-carbonitrile,
6-{[1-Methyl-4-(trifluoromethyl)-1H-pyrazol-3-yl]amino}-4-(6-methylpyridin-2-yl)-1H-pyrrolo[2,3-b]pyridine-3-carbonitrile,
6-[(1-Methyl-1H-pyrazol-3-yl)amino]-4-(5-methylpyridin-3-yl)-1H-pyrrolo[2,3-b]pyridine-3-carbonitrile, or
6-[(1,4-Dimethyl-1H-pyrazol-3-yl)amino]-4-(2-methylpyridin-4-yl)-1H-pyrrolo[2,3-b]pyridine-3-carbonitrile,
or pharmaceutical salt thereof.

The above mentioned compounds may be in a composition as the sole active ingredient or in combination with other active ingredients. Additionally, one or more pharmaceutically acceptable carriers or diluents may be in the composition.

The compounds of the present invention may have one or more asymmetric centres and it is intended that any optical isomers (i.e. enantiomers or diastereomers) as separated, pure or partially purified optical isomers and any mixtures thereof including racemic mixtures, i.e. a mixture of stereoisomers, are included within the scope of the invention.

In this context is understood that when specifying the enantiomeric form, the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In the present context, "pharmaceutically acceptable salts" include pharmaceutically acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

The term "aromatic" refers to a cyclic moiety having a conjugated unsaturated (4n+2)π electron system (where n is a positive integer), sometimes referred to as a delocalized π electron system. The term "heteroaromatic" intents to indicate an aromatic ring structure with one or more heteroatoms. Examples may include pyridinyl and pyrimidinyl.

In the present context, "alkyl" is intended to indicate a straight or branched saturated hydrocarbon. In particular, $C_{1-6}$-alkyl is intended to indicate such hydrocarbon having 1, 2, 3, 4, 5 or 6 carbon atoms and likewise $C_{1-3}$-alkyl is intended to indicate a hydrocarbon having 1, 2 or 3 carbon atoms. Typical alkyl groups include, but are not limited to, methyl, ethyl, propyl, isopropyl, butyl, isobutyl, t-butyl, pentyl, isopentyl, hexyl and the like.

The term "alkoxy" as used herein refers to a group of formula —O— alkyl, wherein alkyl is defined as above. In particular, $C_1$-$C_6$-alkoxy is intended to indicate such hydrocarbon having 1, 2, 3, 4, 5 or 6 carbon atoms and likewise $C_1$-$C_3$-alkoxy indicate is intended to indicate a hydrocarbon having 1, 2 or 3 carbon atoms. Examples of alkoxy groups include, but are not limited to, methoxy, ethoxy, propoxy, butoxy, isobutoxy, t-butoxy, pentoxy, isopropoxy and the like.

The term "alkylamine" or "alkoxyamine" is intended to refer to an amine in the form of $RNH_2$ wherein R is an alkyl or alkoxy group as defined hereinabove.

In the present context, "halogen" is intended to indicate members of the $7^{th}$ main group of the periodic table of the elements, such as fluoro, chloro, bromo and iodo.

"Heteroatom" is intended to mean sulfur, oxygen or nitrogen.

The term "cyclic" as used herein refers to any cyclic structure, including alicyclic, heterocyclic, aromatic and heteroaromatic non-fused ring systems. The term "membered" is meant to denote the number of skeletal atoms that constitute the ring. Thus, for example, pyridinyl, pyranyl, and pyrimidinyl are six-membered rings and pyrrolyl, tetrahydrofuranyl, and thiophenyl are five-membered rings.

The terms "heterocycle", "heterocyclic" and "heterocyclyl" as used herein, alone or in combination, refers to saturated or unsaturated nonaromatic rings containing from 5 to 6 ring atoms where one or more of the ring atoms are heteroatoms.

In some embodiments of the invention a heterocylic ring is intended to mean a 5 or 6 membered cyclic ring structure with 1 or 2 heteroatom(s).

The terms "substituents" or "substituted" as used herein, alone or in combination, refer to groups which may be used to replace hydrogen.

In the present context, the term "therapeutically effective amount" of a compound is intended to indicate an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, e.g. by constructing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease from which the patient is suffering, such as administration of the active compound to alleviate the symptoms or complications, to delay the progression of the disease, to alleviate or relief the symptoms and complications, and/or to cure or eliminate the disease. The patient to be treated is preferably a mammal, in particular a human being. In the present context, "disease" can be used synonymous with disorder, condition, malfunction, dysfunction and the like.

As established above, LRRK2 inhibitors may be used in the treatment of Parkinson's disease and particular mention is made of Parkinson's disease associated with mutations in LRRK2, such as Gly2019Ser. Moreover, LRRK2 inhibitors are also expected to be useful in the treatment of other diseases which are associated with LRRK2. LRRK2 has been identified as a core component in Lewy bodies and is thus expected to be useful in the treatment of Lewy body dementia [*Neuropathol. Appl. Neurobiol.,* 34, 272-283, 2008]. Expression of LRRK2 mRNA is highly enriched in brain, lungs, kidney, spleen and blood suggesting that functional impact of increased LRRK2 activity is likely to be most relevant in pathogenic and pathologic conditions associated with those regions. Support for that notion can be found in studies showing an increased risk of non-skin cancer in LRRK2 Gly2019Ser mutation carriers and especially for renal and lung cancer [*Mov. Disorder,* 25, 2536-2541, 2010]. Over-expression of LRRK2 by chromosomal amplification has also been identified in papillary renal and thyroid carcinomas. Also, genetic association of LRRK2 has been reported for diseases where aberrant responses of the immune system are involved. This is the case for inflammatory bowel diseases such as Crohn's disease and ulcerative colitis as well as for leprosy [*Nat Genet.* 42, 1118-1125, 2010; *Inflamm. Bowel. Dis.* 16, 557-558, 2010; *N Engl. J Med.* 361, 2609-2618, 2009; *Inflamm. Bowel. Dis.* doi: 10.1002/ibd.21651, 2011].

Thus, the compounds, as outlined in formula A hereinabove, or compositions comprising said compounds may be used in treatment of a disease or disorder characterised by over-expression of LRRK2 or a mutated form of LRRK2 such as G2019S, I2020T, M1646T, G2385R, A419V, N551K, R1398H, K1423K, R1441G, R1441H, R1441C, R1628P, S1647T, Y1699C, I2020T or Y2189C.

The disease or disorder may be a CNS disease selected from Lewy body dementia or Parkinson's disease, such as idiopathic Parkinson's disease or sporadic Parkinson's disease or in a Parkinson's disease patient carrying any one of the above mentioned LRRK2 mutations, in particular the G2019S mutation.

In a further embodiment, the compounds, as outlined in formula A hereinabove, or compositions comprising said compounds may be used in the treatment of cancer or an immune related disorder characterised by over-expression of LRRK2 or a mutated form of LRRK2 such as G2019S, I2020T, M1646T, G2385R, A419V, N551K, R1398H, K1423K, R1441G, R1441H, R1441C, R1628P, S1647T, Y1699C, I2020T or Y2189C.

The cancer diseases may reside in the brain, lungs, kidney and spleen or blood organs such as renal cancer, lung cancer, skin cancer, and papillary renal and thyroid carcinomas.

The immune related disorder may in one embodiment be Crohn's disease, ulcerative colitis or leprosy.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $22^{nd}$ Edition, Pharmaceutical Press, 2012. In the present context, "excipient", "carrier", "diluent", "adjuvant" and the like are used synonymously and are intended to mean the same.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragées, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by compression of the mixture in a conventional tabletting machine. Examples of adjuvants or diluents comprise corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Preparation of the Compounds of the Invention

The compounds of the present invention of the general formula A herein above wherein R1 to R4 and L are as defined above can be prepared by the methods outlined in the following reaction schemes and examples. In the described methods it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

The products of the invention can be prepared by the following general methods:

Compounds of formula I or salts thereof with R3 being a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 $C_1$-$C_3$ alkyl, 1 or 2 $C_1$-$C_3$ alkoxy or trifluoromethyl; L is absent or represents $CH_n$, n=1 or 2; R4 represents H, $NH_2$ or a 5 or 6 membered heterocyclic ring with 1 or 2 heteroatoms(s) selected from N or O, which heterocyclic ring is optionally substituted with C1-C3 alkyl, C2-C3 oxy, C1-C3 alkyl amine or C2-C3 alkoxy amine, may be prepared by the following procedures.

a) Reacting a compound of formula II by means of a cross-coupling reaction, such as a Suzuki coupling or other transition metal-catalysed cross-coupling reactions as described in (D. W. Knight, "Coupling Reactions Between sp2 Carbon Centres" in Comprehensive Organic Synthesis, Vol. 3, pp. 481-520, Pergamon Press, 1991), with a boronic acid ($R3B(OH)_2$)

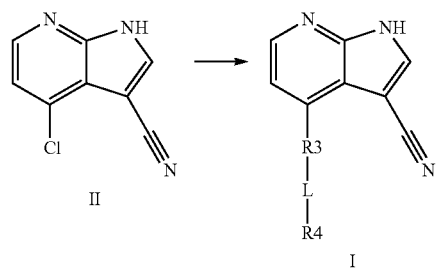

or a corresponding boronic acid ester, where R3 represents for example 3-methoxyphenyl, in a suitable solvent such as a mixture of 1,4-dioxane and water in the presence of a suitable catalyst such as bis(tri-tert-butylphosphine)palladium(0) and a suitable base such as potassium fluoride at a suitable temperature from 60-150° C. The heating could be performed in a microwave system.

b) Step 1: Attachment of a protecting group (P) such as phenylsulfonyl to a compound of formula II utilising standard chemical transformations known to a person skilled in the art, such as reacting formula II with phenylsulfonyl chloride in a suitable solvent such as dichloromethane, in the presence of a base such as triethylamine and a catalyst such as 4-dimethylaminopyridine at an appropriate temperature such as ambient temperature to give a compound of formula III.

Step 2: Reacting a compound of formula III by means of a cross-coupling reaction, such as Suzuki coupling, or other transition metal-catalysed cross-coupling reaction, with an optionally protected boronic acid ($R3B(OH)_2$) or a corresponding boronic acid ester, such as 1-(triisopropylsilyl)pyrrol-3-ylboronic acid, in a suitable solvent such as a mixture of tetrahydrofuran and water in the presence of a suitable catalyst such as [1,1'-bis(di-tert-butylphosphino)-ferrocene]palladium(II) dichloride and a suitable base such as potassium carbonate at a suitable temperature from 60-150° C. The heating could be performed in a microwave system.

Step 3: Reacting a compound of formula IV with aqueous formaldehyde solution in a solvent such as ethanol, followed by an amine such as morpholine, and heating at a suitable temperature from 60-150° C. The heating could be performed in a microwave system.

Step 4: Removal of a protecting group from a compound of formula V, using standard chemical transformations known to a person skilled in the art. This includes hydrolysis of a compound of formula V where P is phenylsulfonyl, in a mixture of water and another suitable solvent such as tetrahydrofuran, in the presence of a catalyst such as potassium carbonate at a suitable temperature from 60-150° C. The heating could be performed in a microwave system.

acid, followed by a reducing agent such as sodium triacetoxyborohydride and heating at a suitable temperature such as ambient.

Step 7: Removal of a protecting group from a compound of formula V, using standard chemical transformations known to a person skilled in the art. This includes hydrolysis of a compound of formula V where P is phenylsulfonyl in a mixture of water and another suitable solvent such as tetrahydrofuran, in the presence of a catalyst such as potassium carbonate at a suitable temperature from 60-150° C. The heating could be performed in a microwave system.

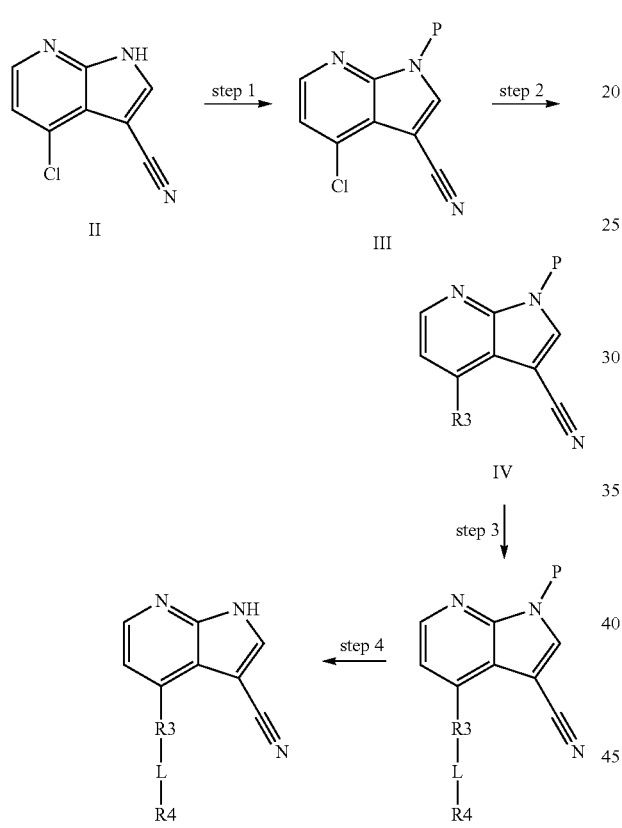

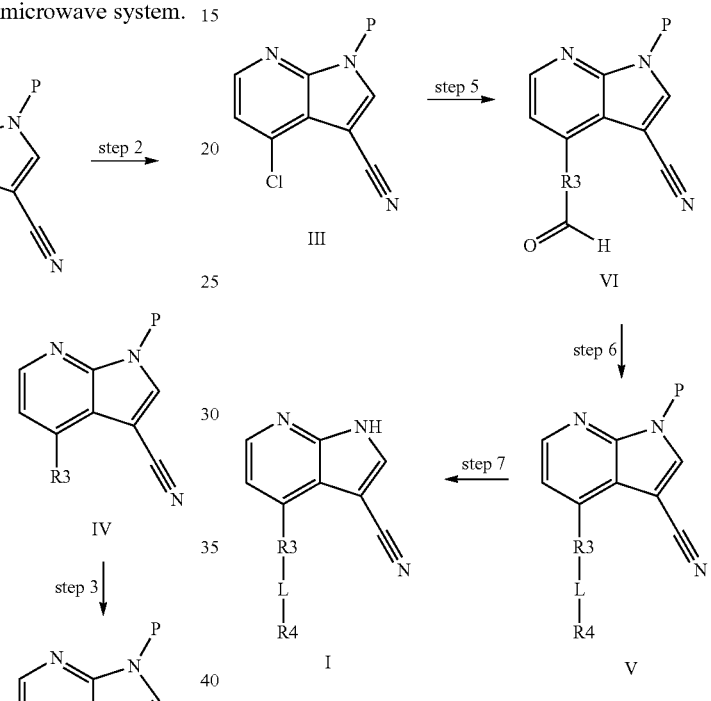

c) Step 5: Reacting a compound of formula III as prepared in step 1 above by means of a cross-coupling reaction, such as Suzuki coupling, or other transition metal-catalysed cross-coupling reaction, with an optionally-substituted formyl-substituted boronic acid (R3B(OH)$_2$) or a corresponding boronic acid ester, such as 4-formyl-3-methylphenylboronic acid, in a suitable solvent such as a mixture of tetrahydrofuran and water in the presence of a suitable catalyst such as [1,1'-bis(di-tert-butylphosphino)-ferrocene]palladium (II) dichloride and a suitable base such as potassium carbonate at a suitable temperature from 60-150° C. The heating could be performed in a microwave system.

Step 6: Reacting a compound of formula VI with an amine such as morpholine, in a suitable solvent such as dichloromethane and a catalyst such as acetic Compounds of formula X or salts thereof with R3 being a 5 or 6 membered aromatic ring or a 5 or 6 membered heteroaromatic ring with 1 or 2 heteroatoms(s) selected from S or N; L is CH$_2$, R4 represents NH$_2$, NMe$_2$ or a 5 or 6 membered heterocyclic ring with 1 or 2 heteroatoms(s) selected from N and/or O, which heterocyclic ring is optionally substituted with C1-C3 alkyl, C2-C3 oxy, C1-C3 alkyl amine or C2-C3 alkoxy amine; R5 represents H or C1-C3 alkyl, may be prepared by the following procedures.

Step 8: Reacting a compound of formula III as prepared above by means of a cross-coupling reaction, such as Suzuki coupling, or other transition metal-catalysed cross-coupling reaction, with an X-, formyl-disubstituted aryl boronic acid (XHCOR3B(OH)2) (X=Cl, Br or I) or a corresponding boronic acid ester, such as 3-chloro-4-formyl-3-phenylboronic acid, in a suitable solvent such as a mixture of tetrahydrofuran and water in the presence of a suitable catalyst such as [1,1'-bis(di-tert-butylphosphino)-ferrocene]palladium(II) dichloride and a suitable base such as potassium carbonate at a suitable temperature from 60-150° C. The heating could be performed in a microwave system.

Step 9: Reacting a compound of formula VII by means of a cross-coupling reaction such as a Heck reaction, or other transition metal catalysed cross-coupling reaction with an vinyl boroxane (R5CH:CHBO)₃, such as 2,4,6-trivinylcyclotriboroxane-pyridine complex, in the presence of a suitable catalyst such as tetrakis(triphenylphosphine)palladium(0) with a suitable base such as potassium carbonate, in a suitable solvent mixture such as 1,2-dimethoxyethane and water, and an appropriate temperature from 60-180° C. The heating could be performed in a microwave system.

Step 10: Reacting a compound of formula VIII with an amine such as morpholine, in a suitable solvent such as dichloromethane and a catalyst such as acetic acid, followed by a reducing agent such as sodium triacetoxyborohydride and heating at a suitable temperature such as ambient.

Step 11: Reacting a compound of formula IX with hydrogen gas at an appropriate pressure such as ambient in a suitable solvent such as methanol, in the presence of a catalyst such as 10% palladium on carbon:

a) Step 12: Reacting a compound of formula II with an oxidising agent such as meta-chloroperoxybenzoic acid in a suitable solvent such as chloroform, at an appropriate temperature such as −20° C. to ambient, over a suitable time such as 16 hours, followed by treatment with methanesulfonic acid.

Step 13: Reacting a suspension of the methanesulfonic acid salt of a compound of formula XI in a suitable solvent such as acetonitrile with dimethyl sulphate, heating at a suitable temperature such as 40-70° C. and subsequent treatment with concentrated ammonia in methanol and heating in a sealed tube at an appropriate temperature such as 40-70° C.

Step 14: Reacting a compound of formula XII by means of a cross-coupling reaction, such as Suzuki coupling, or other transition metal-catalysed cross-coupling reactions as described in [D. W. Knight, "Coupling Reactions Between sp2 Carbon Centres" in Comprehensive Organic Synthesis, v. 3, pp. 481-520, Pergamon Press, 1991, with a boronic acid (R3B(OH)₂) or a corresponding boronic acid ester, where R3 represents for example phenyl, in a suitable solvent such as a mixture of 1,4-dioxane and water in the presence of a suitable catalyst such as bis(tri-tert-butylphosphine)palladium(0) and a suitable base such as potassium fluoride at a suitable temperature from 60-150° C. The heating could be performed in a microwave system.

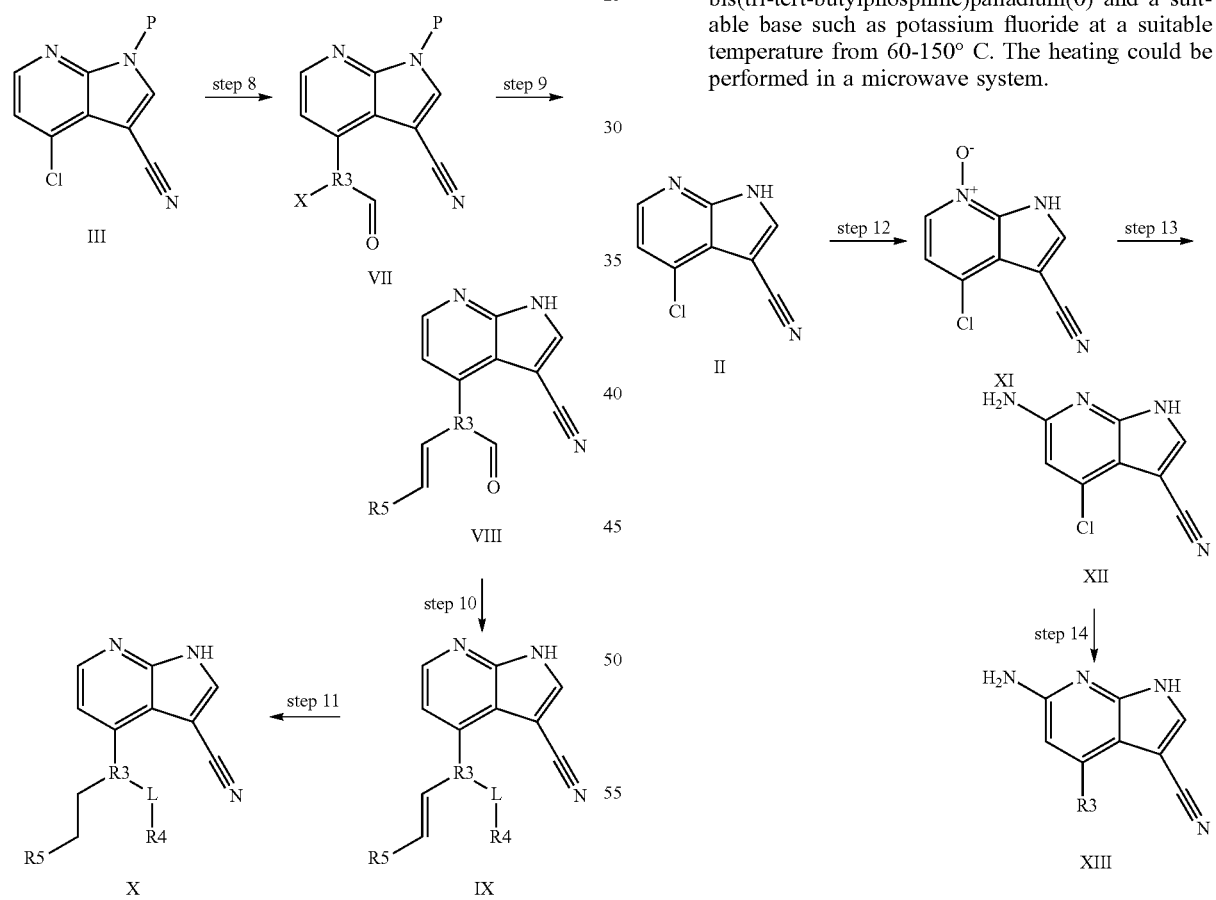

Compounds of formula XIII or salts thereof with R3 being a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 C₁-C₃ alkyl, 1 or 2 C1-C3 alkoxy or trifluoromethyl, may be prepared by the following procedures.

b) Step 15: Reacting the methanesulfonic acid salt of a compound of formula XI as prepared above in an appropriate solvent such as dimethyl formamide with methanesulfonyl chloride, and heating at a suitable temperature of 60-100° C.

Step 16: Attachment of a protecting group (P) such as phenylsulfonyl to a compound of formula XIV utilising standard chemical transformations known to a person skilled in the art, such as reacting formula XIV with phenylsulfonyl chloride in a suitable solvent such as dichloromethane, in the presence of a base such as triethylamine and a catalyst such as 4-dimethylaminopyridine at an appropriate temperature such as ambient temperature to give a compound of formula XV.

Step 17: Reacting a compound of formula XV by means of a cross-coupling reaction, such as Buchwald coupling, or other transition metal-catalysed cross-coupling reactions, with a benzylic amine (RCH$_2$NH$_2$) where R represents for example phenyl, in a suitable solvent such as a dimethyl formamide in the presence of a suitable catalyst such as tris(dibenzylidineacetone)dipalladium(0), phosphine ligand such as 4,5-bis(diphenylphosphino)-9,9-dimethylxanthene and a suitable base such as sodium tert-butoxide at a suitable temperature from 60-150° C. The heating could be performed in a microwave system.

Step 18: Reacting a compound of formula XVI by means of a cross-coupling reaction, such as Suzuki coupling, or other transition metal-catalysed cross-coupling reactions as with a boronic acid (R3B(OH)$_2$) or a corresponding boronic acid ester, where R3 represents for example 3-methylphenylboronic acid, in a suitable solvent such as a mixture of 1,4-dioxane and water in the presence of a suitable catalyst such as bis(tri-tert-butylphosphine)palladium(0) and a suitable base such as potassium fluoride at a suitable temperature from 60-150° C. The heating could be performed in a microwave system.

Step 19: Reaction of a compound of formula XVII in a suitable solvent such as ethanol with hydrogen gas at a suitable temperature and pressure such as ambient, in the presence of a catalyst such as 10% palladium on carbon.

Compounds of formula XIX or salts thereof with R2 representing a 5 or 6 membered heteroaromatic ring with 1 or 2 N, which heteroaromatic ring is optionally substituted with C$_1$-C$_3$ alkyl, C$_1$-C$_3$ fluoroalkyl, halo, C$_1$-C$_3$ alkoxy, C$_1$-C$_3$ alkylamine or C$_1$-C$_3$ alkoxy amine, R3 being a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 C$_1$-C$_3$ alkyl, 1 or 2 C$_1$-C$_3$ alkoxy or trifluoromethyl, may be prepared by the following procedures.

a) Step 20: Reacting a compound of formula XIV as prepared above by means of a cross-coupling reaction, such as Buchwald coupling, or other transition metal-catalysed cross-coupling reactions, with an amine (R2NH$_2$) where R2 represents for example (1-methyl-1H-pyrazol-3-yl), in a suitable solvent such as a dimethyl formamide in the presence of a suitable catalyst such as tris(dibenzylidineacetone)dipalladium(0), an appropriate phosphine ligand such as 4,5-bis(diphenylphosphino)-9,9-dimethylxanthene and a suitable base such as sodium tert-butoxide at a suitable temperature from 60-150° C. The heating could be performed in a microwave system.

Step 21: Reacting a compound of formula XVIII by means of a cross-coupling reaction, such as Suzuki coupling, or other transition metal-catalysed cross-coupling reactions as with a boronic acid (R3B(OH)$_2$) or a corresponding boronic acid ester, where R3 represents for example phenyl, in a suitable solvent such as a mixture of 1,4-dioxane and water in the presence of a suitable catalyst such as bis(tri-tert-butylphosphine)palladium(0) and a suitable base such as potassium fluoride at a suitable temperature from 60-150° C. The heating could be performed in a microwave system.

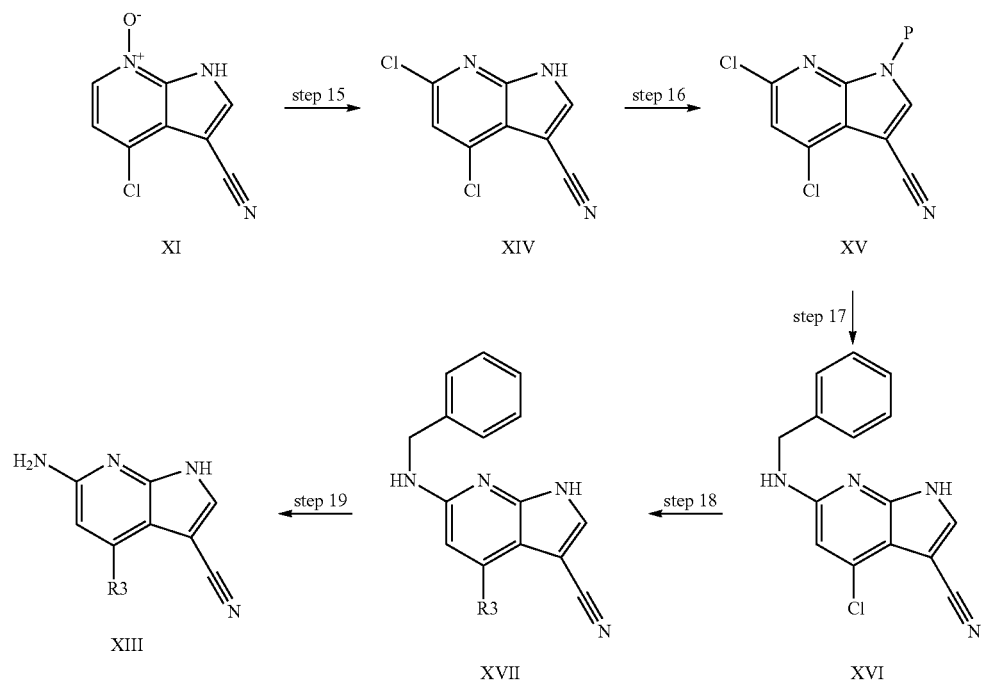

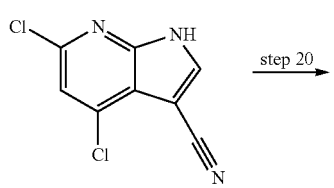

XIV

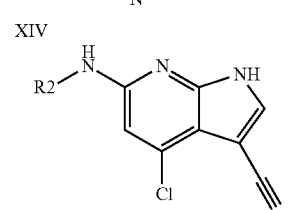

XVIII

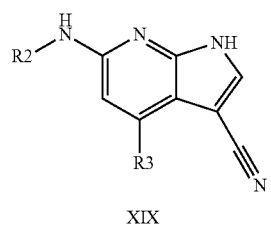

XIX b) Step 22: Reacting a compound of formula XIV with sodium iodide and acetyl chloride in a suitable solvent such as acetonitrile and at an appropriate temperature from ambient to 80° C., to give a compound of formula XX.

Step 24: Reacting a compound of formula XXI by means of a cross-coupling reaction, such as Stille coupling, or other transition metal-catalysed cross-coupling reaction, with an optionally substituted tri-n-butylstannane (R3Sn(Bu)$_3$), such as 4-methyl-2-(tributylstannyl)pyridine, in a suitable solvent such as 1,4-dioxane, in the presence of a catalyst such as tetrakis(triphenylphosphine)palladium(0) and copper iodide in the presence of lithium chloride, at a suitable temperature from 60-150° C. The heating could be performed in a microwave system.

Step 25: Reacting a compound of formula XXII by means of a cross-coupling reaction, such as Buchwald coupling, or other transition metal catalyzed cross-coupling reactions, with an aryl amine R2NH$_2$, in a suitable solvent such as toluene in the presence of a suitable catalyst such as tris(dibenzylideneacetone)dipalladium(0), phosphine ligand such as 4,5-bis(diphenylphosphino)-9,9-dimethylxanthene (Xantphos) and a suitable base such as sodium tert-butoxide at a suitable temperature from 60-150° C. The heating could be performed in a microwave system.

Step 26: Removal of a protecting group from a compound of formula XXIII, using standard chemical transformations known to a person skilled in the art, such as reacting with tetra-n-butylammonium fluoride in a suitable solvent such as tetrahydrofuran at an appropriate temperature from 0-100° C., to give a compound of formula XIX

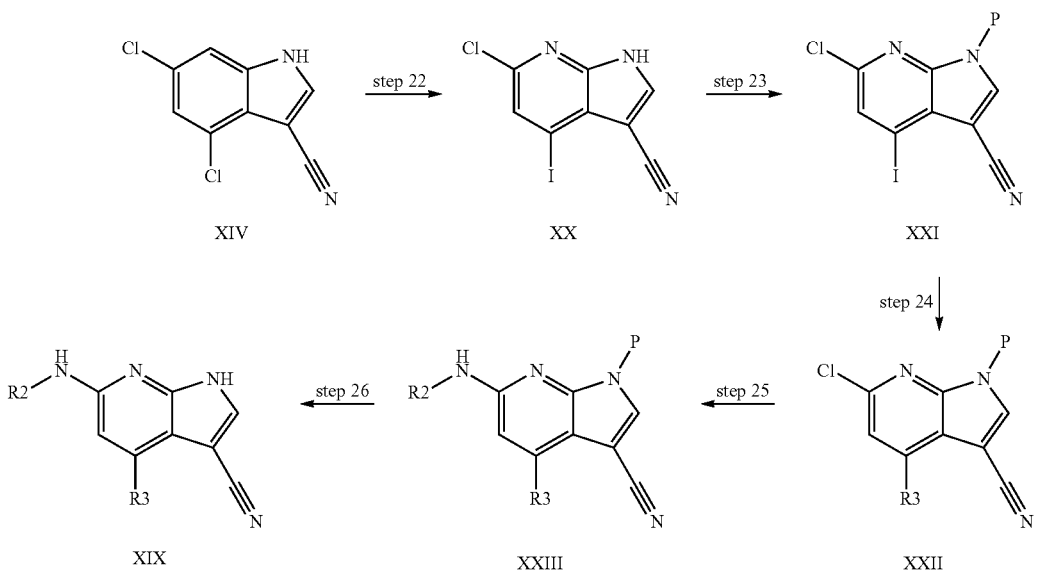

Step 23: Attachment of a protecting group (P) such as 2-(trimethylsilyl)ethoxy]methyl (SEM) to a compound of formula XX utilising standard chemical transformations known to a person skilled in the art, such as reacting formula XX with 2-(trimethylsilyl)ethoxymethyl chloride in a suitable solvent such as dimethyl formamide, in the presence of a base such as sodium hydride at an appropriate temperature from −20° C. to ambient, to give a compound of formula XXI.

c) Step 27: Reacting a compound of formula XX by means of a cross-coupling reaction as described above, to give a compound of formula XXIV.

Step 28: Attachment of a protecting group (P) such as 2-(trimethylsilyl)ethoxy]methyl (SEM) to a compound of formula XXIV as described above, to give a compound of formula XXII, which can be transformed to compounds of formula XIX as described above.

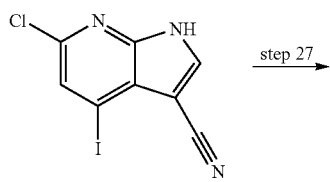

XX

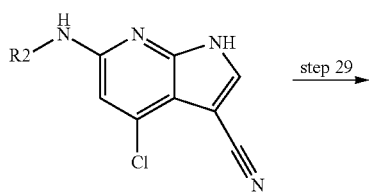

XVIII

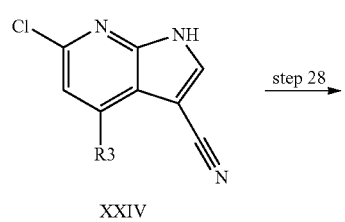

XXIV

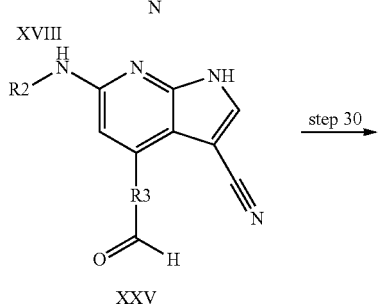

XXV

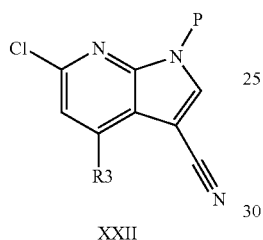

XXII

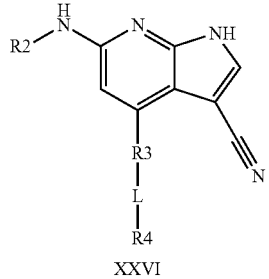

XXVI

Compounds of formula XXVI or salts thereof with R2 representing a 5 or 6 membered heteroaromatic ring with 1 or 2 N, which heteroaromatic ring is optionally substituted with $C_1$-$C_3$ alkyl, $C_1$-$C_3$ alkoxy, $C_1$-$C_3$ alkylamine or $C_1$-$C_3$ alkoxy amine, with R3 being a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 $C_1$-$C_3$ alkyl, 1 or 2 $C_1$-$C_3$ alkoxy or trifluoromethyl, L represents $CH_n$ (n=1 or 2), and R4 represents H, $NH_2$ or a 5 or 6 membered heterocyclic ring with 1 or heteroatom(s) selected from N or O, which heterocyclic ring is optionally substituted with $C_1$-$C_3$ alkyl, $C_2$-$C_3$ alkoxy, $C_1$-$C_3$ alkylamine or $C_2$-$C_3$ alkoxy amine, may be prepared by the following procedures.

Step 29: Reacting a compound of formula XVIII as prepared above by means of a cross-coupling reaction, such as Suzuki coupling, or other transition metal-catalysed cross-coupling reactions with a formyl-substituted boronic acid (HCO—R3B(OH)2) or a corresponding boronic acid ester, where R3 represents for example phenyl, in a suitable solvent such as a mixture of 1,4-dioxane and water in the presence of a suitable catalyst such as bis(tri-tert-butylphosphine)palladium (0) and a suitable base such as potassium fluoride at a suitable temperature from 60-150° C. The heating could be performed in a microwave system.

Step 30: Reacting a compound of formula XXV with an amine such as morpholine, in a suitable solvent such as dichloromethane and a catalyst such as acetic acid, followed by a reducing agent such as sodium triacetoxyborohydride and heating at a suitable temperature such as ambient.

General Methods

Microwave heating was performed with a CEM Discover instrument.

The compounds of the present invention were characterised by high performance liquid chromatography-mass spectroscopy (LC-MS) using one of Methods A-F, and proton nuclear magnetic resonance ($^1$H NMR) spectroscopy.

LC-MS Method A

Instruments: Agilent HP1100 with DAD and MSD G1946 D (positive and negative ionisation, scanning range: 150-1000 Da) or Agilent HP1200 with DAD and MSD 6140 (positive and negative ionisation, scanning range: 150-1000 Da). UV detection was at 230 nm, 254 nm and 270 nm. The conditions and methods are identical for both instruments.

Column: Gemini NX 5 μm C18, 30×2.1 mm, from Phenomenex. Temperature: 40° C.

Mobile phase: Solvent A: Water/10 mM ammonium formate/0.08% (v/v) formic acid pH=3.5.

Solvent B: Acetonitrile/5.3% (v/v) Solvent A/0.08% (v/v) formic acid.

Injection volume: 1 μL

Gradient:

| Time (min) | Solvent A (%) | Solvent B (%) | Flow Rate (ml min$^{-1}$) |
|---|---|---|---|
| 0.00 | 95 | 5 | 1 |
| 0.25 | 95 | 5 | 1 |
| 2.5 | 5 | 95 | 1 |
| 2.55 | 5 | 95 | 1.7 |
| 3.60 | 5 | 95 | 1.7 |
| 3.65 | 5 | 95 | 1 |
| 3.70 | 95 | 5 | 1 |
| 3.75 | 95 | 5 | 1 |

LC-MS Method B

Instrument: Agilent 1200 SL series connected to an Agilent MSD 6140 single quadrupole with a multimode source (ESI/APCI, positive and negative mode ionisation, scanning range 150-850 Da). UV detection was at 230 nm, 254 nm and 270 nm.

Column: Kinetex C18, 2.6 microns, 50×2 mm, from Phenomenex. Temperature: 55° C.

Mobile phase: Solvent A: Water/10 mM ammonium formate/0.08% (v/v) formic acid pH=3.5.
  Solvent B: Acetonitrile/5.3% (v/v) Solvent A/0.08% (v/v) formic acid.

Injection volume: 1 μL.

Gradient:

| Time (min) | Solvent A (%) | Solvent B (%) | Flow Rate (ml min$^{-1}$) |
| --- | --- | --- | --- |
| 0.00 | 95 | 5 | 1.3 |
| 0.12 | 95 | 5 | 1.3 |
| 1.30 | 5 | 95 | 1.3 |
| 1.35 | 5 | 95 | 1.6 |
| 1.85 | 5 | 95 | 1.6 |
| 1.90 | 5 | 95 | 1.3 |
| 1.95 | 95 | 5 | 1.3 |

LC-MS Method C

Column: BEH C18, 1.7 microns, 50×2.1 mm from Acquity Temperature: 55° C.

Mobile phase: Solvent A: Water/0.1% (v/v) formic acid.
  Solvent B: Acetonitrile/0.1% (v/v) formic acid.

Gradient:

| Time (min) | Solvent A (%) | Solvent B (%) | Flow Rate (ml min$^{-1}$) |
| --- | --- | --- | --- |
| 0.00 | 97 | 3 | 0.6 |
| 0.40 | 97 | 3 | 0.6 |
| 3.2 | 2 | 98 | 0.6 |
| 3.8 | 2 | 98 | 0.6 |
| 4.2 | 97 | 3 | 0.6 |
| 4.5 | 97 | 3 | 0.6 |

LC-MS Method D

Column: BEH C18, 1.7 microns, 50×2.1 mm from Acquity Temperature: 55° C.

Mobile phase: Solvent A: Water/0.1% (v/v) formic acid.
  Solvent B: Acetonitrile/0.1% (v/v) formic acid.

Gradient:

| Time (min) | Solvent A (%) | Solvent B (%) | Flow Rate (ml min$^{-1}$) |
| --- | --- | --- | --- |
| 0.00 | 97 | 3 | 0.4 |
| 0.50 | 97 | 3 | 0.4 |
| 1.5 | 10 | 90 | 0.4 |
| 1.8 | 10 | 90 | 0.4 |
| 2.2 | 5 | 95 | 0.4 |
| 3.2 | 5 | 95 | 0.4 |
| 4.0 | 97 | 3 | 0.4 |

LC-MS Method E

Column: XBridge C18, 2.5 microns, 50×4.6 mm Temperature: 35° C.

Mobile phase: Solvent A: Water/0.1% (v/v) formic acid.
  Solvent B: Acetonitrile/0.1% (v/v) formic acid.

Gradient:

| Time (min) | Solvent A (%) | Solvent B (%) | Flow Rate (ml min$^{-1}$) |
| --- | --- | --- | --- |
| 0.00 | 95 | 5 | 1.3 |
| 0.50 | 95 | 5 | 1.3 |
| 1.0 | 85 | 15 | 1.3 |
| 3.3 | 2 | 98 | 1.3 |
| 5.2 | 2 | 98 | 1.3 |
| 5.5 | 95 | 5 | 1.3 |
| 6.0 | 95 | 5 | 1.3 |

LC-MS Method F

Column: XBridge C18, 2.5 microns, 50×4.6 mm Temperature: 35° C.

Mobile phase: Solvent A: 5 mM Ammonium bicarbonate in water (pH 10)
  Solvent B: Acetonitrile Gradient:

| Time (min) | Solvent A (%) | Solvent B (%) | Flow Rate (ml min$^{-1}$) |
| --- | --- | --- | --- |
| 0.00 | 95 | 5 | 1.3 |
| 0.50 | 95 | 5 | 1.3 |
| 1.0 | 85 | 15 | 1.3 |
| 3.3 | 2 | 98 | 1.3 |
| 5.2 | 2 | 98 | 1.3 |
| 5.5 | 95 | 5 | 1.3 |
| 6.0 | 95 | 5 | 1.3 |

$^1$H (400 MHz) nuclear magnetic resonance (NMR) analyses were performed using a Bruker DPX-400 MHz NMR spectrometer. The spectral reference was the known chemical shift of the sample solvent. $^1$H NMR data are reported indicating the chemical shift (δ) as parts per million (ppm), the integration (e.g. 1H), and the multiplicity (s, singlet; d, doublet; t, triplet; q, quartet; sept, septet; m, multiplet; br, broad; dd, doublet of doublets, etc.).

Preparation of Intermediates 1-(Benzenesulfonyl)-4-chloro-1H-pyrollo[2,3-b]pyridine-3-carbonitrile

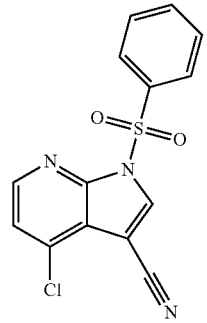 [SMILES: N#Cc1cn(S(=O)(=O)c2ccccc2)c2nccc(Cl)c12]

4-Chloro-1H-pyrollo-[2,3-b]pyridine-3-carbonitrile (3.61 g) was taken up in dichloromethane (120 mL) in a dry round bottomed flask. 4-Dimethylaminopyridine (0.25 g) was added, followed by triethylamine (4.24 mL). Phenylsulfonyl chloride (3.11 ml) was then added, and the reaction was stirred at ambient temperature under nitrogen for 3.5 hours. The reaction mixture was then partitioned between dichloromethane (200 mL) and brine (100 ml). The organic phase was separated, dried over magnesium sulphate and concentrated in vacuo. The residue was triturated from diethyl ether (2×50 mL). The resulting precipitate was filtered and dried under suction to furnish 6.33 g (98%) of a beige solid, identified as 1-(benzenesulfonyl)-4-chloro-1H-pyrollo[2,3-b]pyridine-3-carbonitrile. LC-MS (Method A) (m/z) 318 (MH$^+$); $t_R$=2.59.

1-(Benzenesulfonyl)-4-(1H-pyrrol-3-yl)-1H-pyrrolo[2,3-b]pyridine-3-carbonitrile

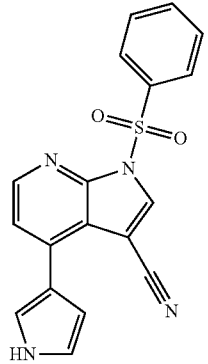 [SMILES: N#Cc1cn(S(=O)(=O)c2ccccc2)c2nccc(-c3cc[nH]c3)c12]

1-(Benzenesulfonyl)-4-chloro-1H-pyrollo[2,3-b]pyridine-3-carbonitrile (0.20 g) was taken up in tetrahydrofuran (4 mL). 1-(Triisopropylsilyl)pyrrol-3-ylboronic acid (0.20 g) was added, followed by water (1 mL) and potassium carbonate (0.26 g). The reaction was degassed with nitrogen and [1,1'-bis(di-tert-butylphosphino)-ferrocene]palladium(II) dichloride (0.020 g) was added and the reaction was further degassed and heated to 100° C. for 1 hour in a sealed microwave process vial. A further 0.10 g of 1-(triisopropylsilyl)pyrrol-3-ylboronic acid was added, followed by [1,1'-bis(di-tert-butylphosphino)-ferrocene]palladium(II) dichloride (0.010 g). The reaction was degassed with nitrogen and heated with microwaves at 100° C. for a further 1 hour. The reaction mixture was then cooled, and partitioned between ethyl acetate (50 mL) and brine (30 mL). The separated organic phase was dried over magnesium sulphate and concentrated in vacuo. The residue was then subjected to silica gel (20 g) column chromatography (hexane to ethyl acetate/hexane (1:1) under gradient elution). The eluted material, obtained as an orange solid (0.087 g, 40%) was identified as 1-(benzenesulfonyl)-4-(1H-pyrrol-3-yl)-H-pyrrolo[2,3-b]pyridine-3-carbonitrile. LC-MS (Method A) (m/z) 349 (MH$^+$); $t_R$=2.5.

1-(Benzenesulfonyl)-4-[1-(morpholin-4-ylmethyl)-1H-pyrrol-3-yl]-1H-pyrrolo[2,3-b]pyridine-3-carbonitrile

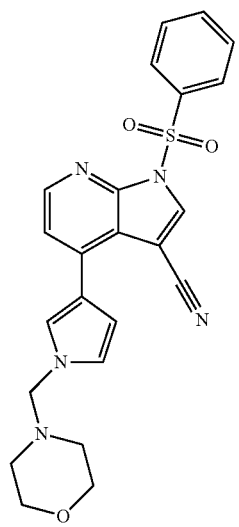 [SMILES: N#Cc1cn(S(=O)(=O)c2ccccc2)c2nccc(-c3ccn(CN4CCOCC4)c3)c12]

1-(Benzenesulfonyl)-4-(1H-pyrrol-3-yl)-H-pyrrolo[2,3-b]pyridine-3-carbonitrile (0.083 g) was taken up in ethanol (10 mL) and formaldehyde (37% aqueous solution, 0.07 mL) was added, followed by morpholine (0.17 mL). The reaction mixture was heated to 110° C. for 2 hours in a microwave process vial. The reaction mixture was then cooled, and concentrated in vacuo. The residue was partitioned between ethyl acetate (50 mL) and brine (30 mL). The separated organic phase was dried over magnesium sulphate and concentrated in vacuo. The residue was then subjected to silica gel (10 g) column chromatography [dichloromethane then ethyl acetate/dichloromethane (1:2) under gradient elution]. The eluted material, obtained as a clear gum (0.029 g, 27%) was identified as 1-(benzenesulfonyl)-4-[1-(morpholin-4-ylmethyl)pyrrol-3-yl]pyrrolo[2,3-b]pyridine-3-carbonitrile. LC-MS (m/z) (Method A) 448 (MH$^+$); $t_R$=2.5.

1-(Benzenesulfonyl)-4-(4-formyl-3-methylphenyl)-1H-pyrrolo[2,3-b]pyridine-3-carbonitrile

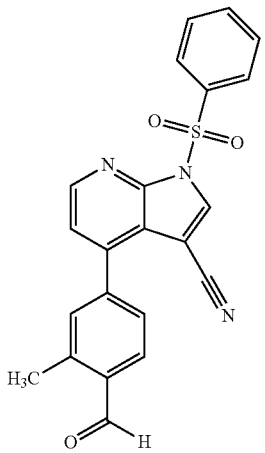 [SMILES: Cc1cc(-c2ccnc3c2c(C#N)cn3S(=O)(=O)c2ccccc2)ccc1C=O]

1-(Benzenesulfonyl)-4-chloro-1H-pyrollo[2,3-b]pyridine-3-carbonitrile (0.40 g) was taken up in tetrahydrofuran (12 mL). 4-Formyl-3-methylphenylboronic acid (0.291 g) was then added, followed by water (3 mL) and potassium carbonate (0.52 g). The reaction mixture was degassed with nitrogen and [1,1'-bis(di-tert-butylphosphino)ferrocene]palladium(II) dichloride (0.04 g) was added. The reaction mixture was then further degassed with nitrogen and heated to 100° C. for 1 hour in a sealed microwave process vial. The cooled reaction mixture was then partitioned between ethyl acetate (150 mL) and brine (100 mL). The separated organic phase was dried over magnesium sulphate and concentrated in vacuo. The residue was then loaded onto a 50 g silica gel column and eluted with hexane then ethyl acetate/hexane (1:2) (gradient elution). The eluted material, obtained as a yellow oil (0.38 g, 75%), was identified as 1-(benzenesulfonyl)-4-(4-formyl-3-methylphenyl)-1H-pyrrolo[2,3-b]pyridine-3-carbonitrile. LC-MS (m/z) (Method A) 402 (MH$^+$); $t_R$=2.68.

1-(Benzenesulfonyl)-4-[3-methyl-4-(morpholin-4-ylmethyl)phenyl]-1H-pyrollo[2,3-b]pyridine-3-carbonitrile

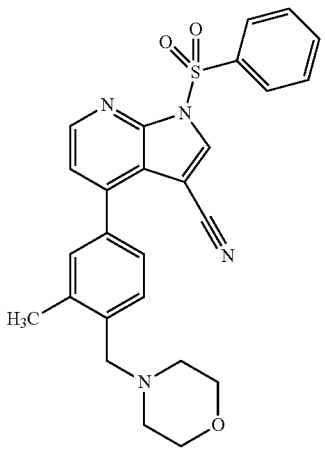 [SMILES: Cc1cc(-c2ccnc3c2c(C#N)cn3S(=O)(=O)c2ccccc2)ccc1CN1CCOCC1]

1-(Benzenesulfonyl)-4-(4-formyl-3-methylphenyl)-1H-pyrrolo[2,3-b]pyridine-3-carbonitrile (0.38 g) and morpholine (0.41 mL) were taken up in dichloroethane (20 mL). Two drops of acetic acid were added to the resulting solution, followed by sodium triacetoxyborohydride (0.60 g). The reaction mixture was stirred at ambient temperature under nitrogen for 24 hours and then partitioned between dichloromethane (150 mL) and brine (100 mL). The organic phase was separated, dried over magnesium sulphate and concentrated in vacuo. The residue was then loaded onto a 50 g silica column and eluted on a gradient from dichloromethane to 1:2 ethyl acetate/dichloromethane to furnish a clear gum (0.40 g, 88%) identified as 1-(benzenesulfonyl)-4-[3-methyl-4-(morpholin-4-ylmethyl)phenyl]-1H-pyrollo[2,3-b]pyridine-3-carbonitrile. LC-MS (Method A) (m/z) 473 (MH$^+$); $t_R$=2.22.

1-(Benzenesulfonyl)-4-(3-chloro-4-formylphenyl)-1H-pyrollo[2,3-b]pyridine-3-carbonitrile

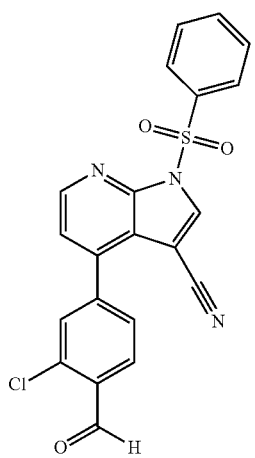 [SMILES: N#Cc1cn(S(=O)(=O)c2ccccc2)c2nccc(-c3ccc(C=O)c(Cl)c3)c12]

The title compound was prepared analogously from Suzuki coupling with 1-(benzenesulfonyl)-4-chloro-1H-pyrollo[2,3-b]pyridine-3-carbonitrile and 3-chloro-4-formylphenylboronic acid to furnish a white solid. Yield: 187 mg, 28%. LC-MS (Method A) (m/z) 422 (MH$^-$); $t_R$=2.7.

4-(3-Ethenyl-4-formylphenyl)-1H-pyrollo[2,3-b]pyridine-3-carbonitrile

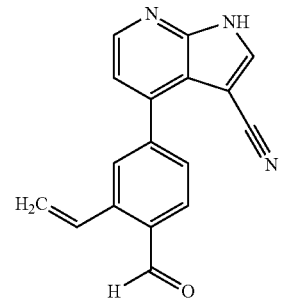 [SMILES: C=Cc1cc(-c2ccnc3[nH]cc(C#N)c23)ccc1C=O]

1-(Benzenesulfonyl)-4-(3-chloro-4-formylphenyl)-1H-pyrollo[2,3-b]pyridine-3-carbonitrile (0.19 g) was taken up in 1,2-dimethoxyethane (7.5 mL) and 2,4,6-trivinylcyclotriboroxane-pyridine complex (0.21 g) was added, followed by potassium carbonate (0.12 g), water (2.5 mL) and tetrakis(triphenylphosphine)palladium(0) (0.025 g). The reaction mixture was degassed with nitrogen and then heated to 180° C. for 2 hours in a sealed microwave process vial. The cooled reaction mixture was then partitioned between ethyl acetate (100 mL) and brine (60 mL). The organic phase was separated, dried over magnesium sulphate and concentrated in vacuo. The reaction mixture was then triturated with acetonitrile, and the resulting precipitate filtered and dried under suction to furnish 0.062 g (51%) of a yellow solid, identified as 4-(3-ethenyl-4-formylphenyl)-1H-pyrollo[2,3-b]pyridine-3-carbonitrile. LC-MS (m/z) (Method A) 274 (MH$^+$); $t_R$=2.25.

4-[3-Ethenyl-4-(morpholin-4-ylmethyl)phenyl]-1H-pyrollo[2,3-b]pyridine-3-carbonitrile

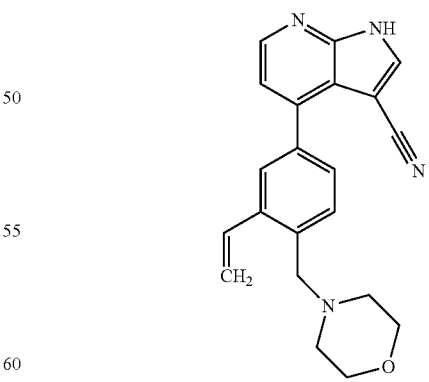

The title compound was prepared by analogy with Example 7 via reductive amination on 4-(3-ethenyl-4-formylphenyl)-1H-pyrollo[2,3-b]pyridine-3-carbonitrile with morpholine, to afford a white solid. Yield: 32 mg, 41%. LC-MS (Method A) (m/z) 345 (MH$^+$); $t_R$=1.8

4-Chloro-1H-pyrrolo[2,3-b]pyridine-3-carbonitrile-7-oxide methanesulfonic acid salt

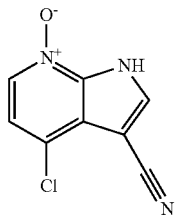 [SMILES: N#Cc1c[nH]c2c1c(Cl)cc[n+]2[O-]]

4-Chloro-1H-pyrrolo[2,3-b]pyridine-3-carbonitrile (3.00 g) was suspended in chloroform (60 mL) and the reaction mixture cooled to 0° C. meta-Chloroperoxybenzoic acid was then added portion-wise over 10 min and the reaction mixture was then stirred at ambient temperature for 16 h. Methanesulfonic acid (1.64 mL) was then added drop wise over ~1 minute. The reaction mixture was then diluted with diethyl ether (60 ml), cooled (ice-water bath) and then stirred for 30 minutes. The resulting precipitate was filtered, and the residue was washed with diethyl ether (3×20 mL). The resulting solid was dried in vacuo (60° C.) for 2 h to give 5.23 g (88%) of a beige solid, identified as 4-chloro-1H-pyrrolo[2,3-b]pyridine-3-carbonitrile-7-oxide methanesulfonic acid salt; LC-MS (Method A) (m/z) 194 (MH+); tR=1.37.

6-Amino-4-chloro-1H-pyrrolo[2,3-b]pyridine-3-carbonitrile

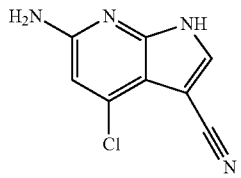 [SMILES: N#Cc1c[nH]c2nc(N)cc(Cl)c12]

4-Chloro-1H-pyrrolo[2,3-b]pyridine-3-carbonitrile-7-oxide methanesulfonic acid salt (2.00 g) was suspended in acetonitrile (15 mL), and dimethyl sulfate (0.79 g) was then added. The suspension was stirred at 60° C. for 16 h, after which a clear-brown solution was formed.

The reaction mixture was cooled to room temperature and transferred into 3×15 mL Ace glass tubes. 7 N Ammonia in methanol (5 mL) was then added to each tube. The sealed tubes were then heated at 70° C. for 48 h. The reaction mixture was then cooled in an ice bath, the contents of each tube combined and concentrated under reduced pressure. The residue was purified by silica-gel flash chromatography [ethyl acetate in isohexane (0-100%), gradient elution]. The eluted material, obtained as an off-white solid 0.053 g (5%), was identified as 6-amino-4-chloro-1H-pyrrolo[2,3-b]pyridine-3-carbonitrile. LC-MS (Method A) (m/z) 193 (MH+); tR=1.79.

4,6-Dichloro-1H-pyrrolo[2,3-b]pyridine-3-carbonitrile

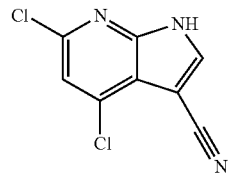 [SMILES: N#Cc1c[nH]c2nc(Cl)cc(Cl)c12]

4-Chloro-1H-pyrrolo[2,3-b]pyridine-3-carbonitrile-7-oxide methanesulfonic acid (5.37 g) was suspended in DMF (50 mL). Methanesulphonyl chloride (10.87 g) was then added, and the reaction mixture was then heated to 80° C. for 10 min, resulting in a pale-brown solution.

The reaction mixture was then cooled and evaporated under reduced pressure. The resulting yellow gum was triturated with dichloromethane. The precipitate was filtered and then dried to afford a light yellow powder (2.72 g, 46%), identified as 4,6-dichloro-1H-pyrrolo[2,3-b]pyridine-3-carbonitrile. LC-MS (Method A) (m/z) 210 (M−H)⁻; tR=1.77.

1-(Benzenesulfonyl)-4,6-dichloro-1H-pyrrolo[2,3-b]pyridine-3-carbonitrile

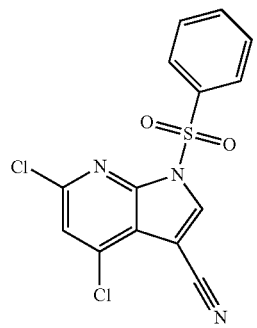 [SMILES: N#Cc1cn(S(=O)(=O)c2ccccc2)c2nc(Cl)cc(Cl)c12]

4,6-Dichloro-1H-pyrrolo[2,3-b]pyridine-3-carbonitrile was suspended in anhydrous dichloromethane (20 mL). Triethylamine (0.290 g) was then added, followed by 4-dimethylaminopyridine (0.023 g). To the reaction mixture was added benzensulfonyl chloride (0.41 g) drop-wise; a clear solution was formed. The reaction mixture was left to stir at rt under N₂ for 2 h, and then evaporated under reduced pressure. The residue was triturated with water; the resulting precipitate was filtered and dried at 60° C. in vacuo to a beige solid (0.56 g, 83%), identified as 1-(benzenesulfony)-4,6-dichloro-1H-pyrrolo[2,3-b]pyridine-3-carbonitrile. LC-MS (Method A) (m/z) 352 (M+); tR=2.74.

6-(Benzylamino)-4-chloro-1H-pyrrolo[2,3-b]pyridine-3-carbonitrile

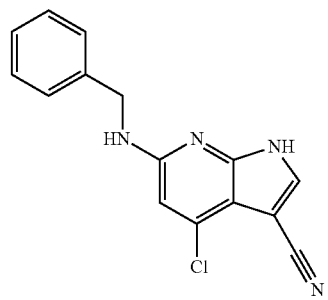 [SMILES: N#Cc1c[nH]c2nc(NCc3ccccc3)cc(Cl)c12]

1-(Benzenesulfonyl)-4,6-dichloro-1H-pyrrolo[2,3-b]pyridine-3-carbonitrile (0.30 g), benzylamine (0.046 g), sodium tert-butoxide (0.40 g), tris(dibenzylideneacetone)dipalladium(0) (0.039 g) and 4,5-bis(diphenylphosphino)-9,9-dimethylxanthene (Xantphos, 0.054 g) added to a microwave vial followed by dry DMF (15 mL). The mixture was flushed with N₂ for ~10 min, and then heated to 120° C. with microwaves for 1 h in a sealed process vial. The reaction mixture was evaporated, and then subjected to silica-gel column chromatography [ethyl acetate-isohexane (0-100%), gradient elution]. The eluted material, obtained as a red solid 0.14 g (59%), was identified as 6-(benzylamino)-4-chloro-1H-pyrrolo[2,3-b]pyridine-3-carbonitrile. LC-MS (Method A) (m/z) 283 (M+H+); tR=2.47.

6-(Benzylamino)-4-(3-methylphenyl-1H-pyrrolo[2,3-b]pyridine-3-carbonitrile

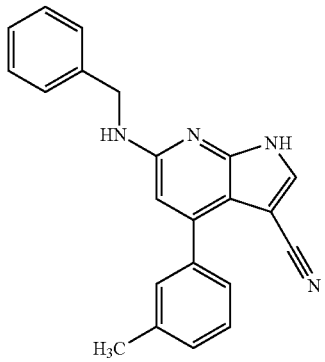 [SMILES: Cc1cccc(-c2cc(NCc3ccccc3)nc3[nH]cc(C#N)c23)c1]

6-(Benzylamino)-4-chloro-1H-pyrrolo[2,3-b]pyridine-3-carbonitrile (0.063 g), 3-methylphenylboronic acid (0.040 g), potassium fluoride (0.026 g) and bis(tri-tert-butylphosphine)palladium (0) (0.006 g) were suspended in 1,4-dioxane:water (6:1, 3.5 mL). The reaction mixture was then stirred at room temperature under a stream of nitrogen for 5 min, and then heated at 120° C. for 60 min in a sealed microwave process vial. After cooling to room temperature, the reaction mixture was diluted with ethyl acetate (20 mL) and water (20 mL), and filtered through Celite. The organic phase was separated, and the aqueous layer was extracted with ethyl acetate (3×20 mL). The combined organic extracts were washed with brine (20 mL), dried over magnesium sulfate and concentrated in vacuo. The residue was subjected to silica-gel flash chromatography [ethyl acetate-isohexane (0-100%), gradient elution]. The eluted material, obtained as a beige solid (0.033 g, 58%), was identified as 6-(benzylamino)-4-(3-methylphenyl-1H-pyrrolo[2,3-b]pyridine-3-carbonitrile. LC-MS (Method A) (m/z) 339 (MH+); tR=2.65.

4-Chloro-6-[1-(1-methyl-1H-pyrazol-3-yl)amino]-1H-pyrrolo[2,3-b]pyridine-3-carbonitrile

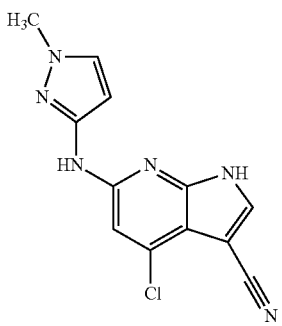 [SMILES: Cn1ccc(Nc2cc(Cl)c3c(C#N)c[nH]c3n2)n1]

4,6-Dichloro-1H-pyrrolo[2,3-b]pyridine-3-carbonitrile (0.118 g), 1-methyl-1H-pyrazol-3-amine (0.027 g), sodium tert-butoxide (0.269 g), tris(dibenzylideneacetone)dipalladium(0) (0.026 g) and 4,5-bis(diphenylphosphino)-9,9-dimethylxanthene (Xantphos, 0.035 g) were added to a microwave vial, followed by dry DMF (5 mL). The reaction mixture was flushed with N₂ for ~10 min, and then heated to 80° C. with microwaves for 1 h. The reaction mixture was subjected to silica-gel flash column chromatography [dichloromethane-methanol (2-3%)]. The eluted material, obtained as a yellow solid (0.055 g, 78%) was identified as 4-chloro-6-[(1-methyl-1H-pyrazol-3-yl)amino]-1H-pyrrolo[2,3-b]pyridine-3-carbonitrile. LC-MS (Method A) (m/z) 273 (M+H+); tR=2.11.

4-(4-Formyl-3-methylphenyl)-6-[1-(1-methylpyrazol-3-yl)amino]-1H-pyrrolo[2,3-b]pyridine-3-carbonitrile

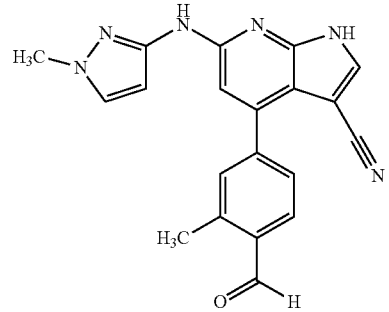 [SMILES: Cc1cc(-c2cc(Nc3ccn(C)n3)nc3[nH]cc(C#N)c23)ccc1C=O]

4-Chloro-6-[(1-methyl-1H-pyrazol-3-yl)amino]-1H-pyrrolo[2,3-b]pyridine-3-carbonitrile (0.030 g), 3-methyl-4-formylphenylboronic acid (0.036 g), potassium fluoride (0.019 g) and bis(tri-tert-butylphosphine)palladium(0) (0.008 g) were suspended in 1,4-dioxane:water (6:1, 3.5 mL) and stirred at room temperature under a stream of with N₂ for 5 min. The reaction mixture was then heated to 120° C. with microwaves for 60 minutes in a sealed process vial. After cooling to room temperature, the reaction mixture was diluted with ethyl acetate (20 mL) and water (20 mL), and filtered through Celite. The organic phase was separated and the aqueous layer was extracted with ethyl acetate (3×20 mL). The combined organic extracts were washed with brine (20 mL), dried over magnesium sulfate and concentrated in vacuo. The residue was subjected to silica-gel flash column chromatography [ethyl acetate-isohexane (0-100%), gradient elution]. The eluted material, obtained as a yellow solid (0.014 g, 35%), was identified as 4-(4-formyl-3-methylphenyl)-6-[(1-methylpyrazol-3-yl)amino]-1H-pyrrolo[2,3-b]pyridine-3-carbonitrile. LC-MS (m/z) (Method B) 357 (MH+); tR=1.10.

4-Chloro-6-[1-(1-methyl-1H-pyrazol-4-yl)amino]-1H-pyrrolo[2,3-b]pyridine-3-carbonitrile

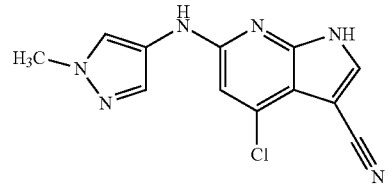 [SMILES: Cn1cc(Nc2cc(Cl)c3c(C#N)c[nH]c3n2)cn1]

4,6-Dichloro-1H-pyrrolo[2,3-b]pyridine-3-carbonitrile (0.100 g), 1-methyl-1H-pyrazol-4-amine (0.080 g), sodium tert-butoxide (0.22584 g), tris(dibenzylideneacetone)dipalladium(0) (0.002 g) and 4,5-bis(diphenylphosphino)-9,9-dimethylxanthene (Xantphos, 0.030 g) were added to a microwave vial, followed by dry DMF (5 mL). The reaction mixture was then flushed with $N_2$ for ~10 min, and then heated to 80° C. for 1 h with microwaves. The reaction mixture was then cooled and filtered through Celite, and the eluted material evaporated under reduced pressure. The resulting light brown solid was triturated with toluene and then dichloromethane. The resulting yellow solid (0.064 g, 50%) was identified as 4-chloro-6-[(1-methyl-1H-pyrazol-4-yl)amino]-1H-pyrrolo[2,3-b]pyridine-3-carbonitrile. LC-MS (Method A) (m/z) 273 (M+H+); tR=1.62.

4-Chloro-6-[(pyridin-2-yl)amino]-1H-pyrrolo[2,3-b]pyridine-3-carbonitrile

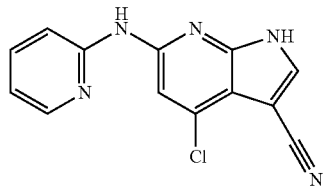 [SMILES: N#Cc1c[nH]c2nc(Nc3ccccn3)cc(Cl)c12]

4,6-Dichloro-1H-pyrrolo[2,3-b]pyridine-3-carbonitrile (0.100 g), 2-aminopyridine (0.022 g), sodium tert-butoxide (0.225 g), tris(dibenzylideneacetone)dipalladium(0) (0.002 g) and 4,5-bis(diphenylphosphino)-9,9-dimethylxanthene (Xantphos, (0.030 g) were added to a microwave vial, followed by dry DMF (5 mL). The reaction mixture was flushed with $N_2$ for ~10 min, and then heated to 80° C. with microwaves for 1 h in a sealed process vial. The reaction mixture was then filtered through Celite, and the eluent concentrated under reduced pressure. The residual brown solid was triturated with dichloromethane, resulting in a beige solid (0.078 g, 62%), identified as 4-chloro-6-[(pyridin-2-yl)amino]-1H-pyrrolo[2,3-b]pyridine-3-carbonitrile. LC-MS (Method A) (m/z) 270 (M+H+); tR=1.24.

6-Chloro-4-iodo-1H-pyrrolo[2,3-b]pyridine-3-carbonitrile

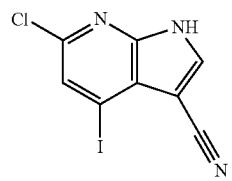 [SMILES: N#Cc1c[nH]c2nc(Cl)cc(I)c12]

To a solution of 4,6-dichloro-1H-pyrrolo[2,3-b]pyridine-3-carbonitrile (2.0 g, 9.43 mmol) in acetonitrile (50.0 mL) was added sodium iodide (2.83 g, 18.86 mmol) and acetyl chloride (1.47 g, 18.86 mmol). The reaction mixture was allowed to stir at 80° C. for 24 h. Another portion of sodium iodide (2.83 g, 18.86 mmol) and acetyl chloride (1.47 g, 18.86 mmol) was then added, and the reaction mixture was allowed to stir at 80° C. for another 24 h. A further portion of sodium iodide (2.83 g, 18.86 mmol) and acetyl chloride (1.47 g, 18.86 mmol) was then added, and the reaction mixture was allowed to stir at 80° C. for a further 24 h (total of 72 h). Water was then added, and the resulting mixture was extracted with ethyl acetate (3×30 mL). The combined organic extracts were dried over anhydrous $Na_2SO_4$ and evaporated under reduced pressure. The residue was purified by SFC, to afford 6-chloro-4-iodo-1H-pyrrolo[2,3-b]pyridine-3-carbonitrile (600 mg, 21.0%) as white solid; LC-MS (Method C) (m/z) 301.79 [M−H]+; tR=2.06 min.

SFC Purification Conditions

Preparative SFC was run on Waters SFC-200 system consisting of auto injector and collector, binary pump 2545Q, UV-Visible detector model: 2489 (operating at 230 nm).

Column: Ethyl pyridine (150×30) mm

Co-solvent Percentage: 15% Methanol

Total Flow: 100 mL/min

ABPR: 150 bar

UV at: 230 nm

Stack time: 3.5 min

Load/inj: 20 mg/inj

Solubility: Methanol:THF (3:1)

6-Chloro-4-iodo-1-{[2-(trimethylsilyl)ethoxy]methyl}-1H-pyrrolo[2,3-b]pyridine-3-carbonitrile

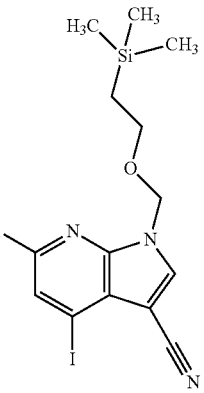

6-Chloro-4-iodo-1H-pyrrolo[2,3-b]pyridine-3-carbonitrile (0.7 g, 2.31 mmol) was taken up in dimethyl formamide (20 mL), and the temperature of the resulting solution was cooled to 0° C. Sodium hydride (50%, 0.14 g, 3.00 mmol) was added, and the reaction mixture was stirred for 10 min. 2-(Trimethylsilyl)ethoxymethyl chloride (0.46 g, 2.77 mmol) was then added, and the reaction mixture was allowed to stir at ambient temperature for 2 h. On completion of the reaction (monitored by TLC), water was added and the mixture was extracted with ethyl acetate (3×30 mL). The combined organic extracts were dried over anhydrous sodium sulfate and evaporated under reduced pressure to afford 6-chloro-4-iodo-1-{[2-(trimethylsilyl)ethoxy]methyl}-1H-pyrrolo[2,3-b]pyridine-3-carbonitrile (900 mg, 90.0%) as an off-white solid; LC-MS (Method C) (m/z) 433.81 [M+H]+; tR=3.19 min.

6-Chloro-4-(4-methylpyridin-2-yl)-1-{[2-(trimethylsilyl)ethoxy]methyl}-1H-pyrrolo[2,3-b]pyridine-3-carbonitrile

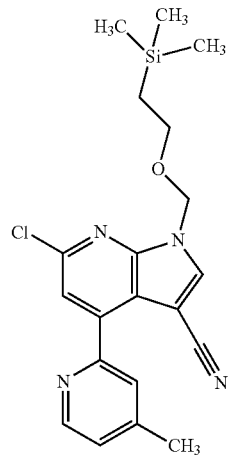 [SMILES: Cc1ccnc(-c2cc(Cl)nc3c2c(C#N)cn3COCC[Si](C)(C)C)c1]

To a solution of 6-chloro-4-iodo-1-{[2-(trimethylsilyl)ethoxy]methyl}-1H-pyrrolo[2,3-b]pyridine-3-carbonitrile (500 mg, 1.15 mmol) and 4-methyl-2-(tributylstannyl)pyridine (441 mg, 1.15 mmol) in 1,4 dioxane (30 mL) were added lithium chloride (97 mg, 2.30 mmol) and copper iodide (10 mg, 0.057 mmol). The reaction mixture was degassed with nitrogen for 20 min and then tetrakis(triphenylphosphine)palladium(0) (66 mg, 0.057 mmol) was added. The reaction mixture in a sealed tube was heated at 90° C. for 18 h. After completion of the reaction (monitored by TLC), the reaction mixture was cooled to ambient temperature, poured into ice-cold water and extracted with ethyl acetate (2×50 mL). The combined organic extracts were washed with saturated brine solution, dried over sodium sulfate and concentrated under reduced pressure. The residue was subjected to column chromatography using silica-gel (100-200 mesh) and eluted with 15% ethyl acetate in petroleum ether to afford 300 mg (yield: 65%) of 6-chloro-4-(4-methylpyridin-2-yl)-1-{[2-(trimethylsilyl)ethoxy]methyl}-1H-pyrrolo[2,3-b]pyridine-3-carbonitrile as a brown solid; LC-MS (Method C) (m/z) 399 [M+H]$^+$; tR=2.97.

The following intermediate of the invention was prepared analogously:

6-Chloro-4-(6-methylpyridin-2-yl)-1-{[2-(trimethylsilyl)ethoxy]methyl}-1H-pyrrolo[2,3-b]pyridine-3-carbonitrile

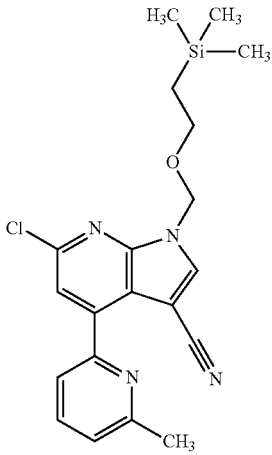 [SMILES: Cc1cccc(-c2cc(Cl)nc3c2c(C#N)cn3COCC[Si](C)(C)C)n1]

300 mg obtained from 6-chloro-4-iodo-1-{[2-(trimethylsilyl)ethoxy]methyl}-1H-pyrrolo[2,3-b]pyridine-3-carbonitrile (500 mg, 1.15 mmol) and 2-methyl-6-(tributylstannyl)pyridine (441 mg, 1.15 mmol) in 65% yield; LC-MS (Method C) (m/z) 399 [M+H]$^+$; tR=3.00.

6-Chloro-4-(2-methylpyridin-4-yl)-1-{[2-(trimethylsilyl)ethoxy]methyl}-1H-pyrrolo[2,3-b]pyridine-3-carbonitrile

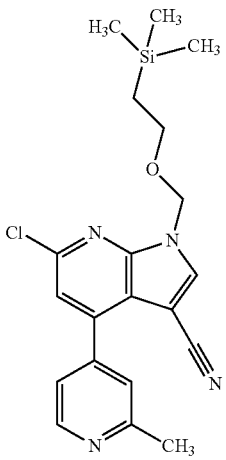

A mixture of 6-chloro-4-iodo-1-{[2-(trimethylsilyl)ethoxy]methyl}-1H-pyrrolo[2,3-b]pyridine-3-carbonitrile (900 mg, 2.07 mmol) and (2-methylpyridin-4-yl)boronic acid (450 mg, 2.07 mmol) in 1,4-dioxane (20.0 mL) and water (4.0 mL) was degassed with nitrogen for 15 min.

Tetrakis(triphenylphosphine)palladium(0) (120 mg, 0.10 mmol) and caesium carbonate (1.01 g, 3.11 mmol) were then added, and the reaction mixture was allowed to stir at 100° C. in a sealed tube for 18 h. On completion of the reaction (monitored by TLC), water was added and the mixture extracted with ethyl acetate (3×30 mL). The combined organic extracts were dried over anhydrous sodium sulfate and evaporated under reduced pressure. The residue was subjected to silica-gel (100-200 mesh) column chromatography, eluted with 30% ethyl acetate in petroleum ether, to afford compound 6-chloro-4-(2-methylpyridin-4-yl)-1-{[2-(trimethylsilyl)ethoxy]methyl}-1H-pyrrolo[2,3-b]pyridine-3-carbonitrile (500 mg, 60%) as an off white solid; LC-MS (Method E) (m/z) 399 [M+H]$^+$; tR=3.81.

6-Chloro-4-(5-methylpyridin-3-yl)-1H-pyrrolo[2,3-b]pyridine-3-carbonitrile

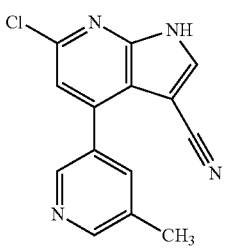 [SMILES: Cc1cncc(-c2cc(Cl)nc3[nH]cc(C#N)c23)c1]

To a solution of 6-chloro-4-iodo-1H-pyrrolo[2,3-b]pyridine-3-carbonitrile (1.5 g, 4.95 mmol) and (5-methylpyridin-3-yl)boronic acid in 1,4 dioxane (10 mL) and water (10 mL) was added potassium fluoride. The reaction mixture was degassed with argon for 15 min. Bis(tri-tert-butylphosphine)palladium(0) was then added, and the reaction mixture was heated at 80° C. for 18 h. After completion of the reaction (monitored by TLC), the reaction mixture was cooled to ambient temperature and filtered through a bed of Celite. The eluent was poured into ice-cold water and extracted with ethyl acetate (3×20 mL). The combined organic extracts were washed with water, dried with sodium sulfate and concentrated under reduced pressure to afford 700 mg (yield: 53%) of 6-chloro-4-(5-methylpyridin-3-yl)-1H-pyrrolo[2,3-b]pyridine-3-carbonitrile as a pale brown solid; $^1$H NMR (DMSO-$d_6$, 400 MHz) δ: 13.20 (1H, s), 8.65 (1H, s), 8.57 (2H, s), 7.92 (1H, s), 7.44 (1H, s) 2.40 (3H, s).

6-Chloro-4-(5-methylpyridin-3-yl)-1-{[2-(trimethylsilyl)ethoxy]methyl}-1H-pyrrolo[2,3-b]pyridine-3-carbonitrile

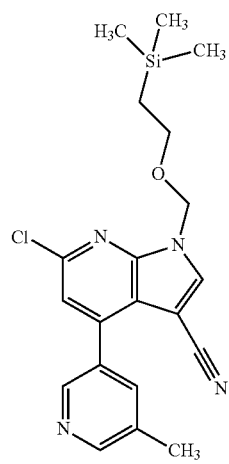 [SMILES: Cc1cncc(-c2cc(Cl)nc3c2c(C#N)cn3COCC[Si](C)(C)C)c1]

To a solution of 6-chloro-4-(5-methylpyridin-3-yl)-1H-pyrrolo[2,3-b]pyridine-3-carbonitrile (0.7 g, 2.61 mmol) in dimethyl formamide (15.0 mL) at 0° C. was added sodium hydride (50%) (0.094 g, 3.91 mmol) and 2-(trimethylsilyl)ethoxymethyl chloride (0.520 g, 3.13 mmol). The reaction mixture was allowed to stir at ambient temperature for 2 h. On completion of the reaction (monitored by TLC), water was added, and the mixture was extracted with ethyl acetate (3×30 mL). The combined organic extracts were dried over anhydrous sodium sulfate and evaporated to afford 6-chloro-4-(5-methylpyridin-3-yl)-1-{[2-(trimethylsilyl)ethoxy]methyl}-1H-pyrrolo[2,3-b]pyridine-3-carbonitrile as off white solid (600 mg, 60%); $^1$H NMR (DMSO-$d_6$, 400 MHz) δ: 8.78 (1H, s), 8.664-8.660 (1H, d, J=1.6 Hz), 8.58 (1H, s), 7.93 (1H, s), 7.54 (1H, s), 5.68 (2H, s), 3.63-3.59 (2H, t, J=8.0 Hz), 2.40 (3H, s), 0.90-0.86 (2H, m), −0.05 (9H, s).

6-{[1-Methyl-4-(trifluoromethyl)-1H-pyrazol-3-yl]amino}-4-(5-methylpyridin-3-yl)-1-{[2-(trimethylsilyl)ethoxy]methyl}-1H-pyrrolo[2,3-b]pyridine-3-carbonitrile

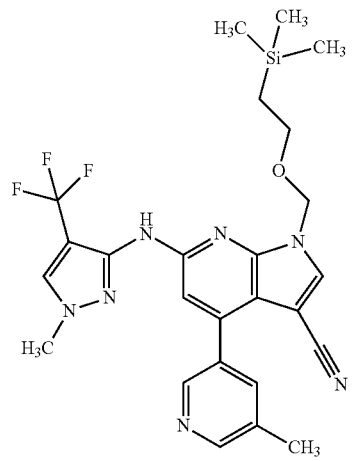 [SMILES: Cc1cncc(-c2cc(Nc3nn(C)cc3C(F)(F)F)nc3c2c(C#N)cn3COCC[Si](C)(C)C)c1]

A mixture of 1-methyl-4-(trifluoromethyl)-1H-pyrazol-3-amine (165 mg, 0.879 mmol) and 6-chloro-4-(5-methylpyridin-3-yl)-1-{[2-(trimethylsilyl)ethoxy]methyl}-1H-pyrrolo[2,3-b]pyridine-3-carbonitrile (350 mg, 0.879 mmol) in 1,4-dioxane (3.0 mL) was degassed with nitrogen for 15 min. Then tris(dibenzylideneacetone)dipalladium(0) (80 mg, 0.08 mmol) was added, followed by 4,5-bis(diphenylphosphino)-9,9-dimethylxanthene (Xantphos) (50 mg, 0.08 mmol) and sodium tert-butoxide (126 mg, 1.31 mmol). The reaction mixture was irradiated in a microwave at 100° C. for 60 min. On completion of the reaction (monitored by TLC), water was added and the reaction mixture was extracted with ethyl acetate (3×30 mL). The combined organic extracts were dried over anhydrous sodium sulfate and evaporated under reduced pressure. The residual material was subjected to silica-gel (100-200 mesh) column chromatography, eluted with 50% ethyl acetate in petroleum ether to afford 6-{[1-methyl-4-(trifluoromethyl)-1H-pyrazol-3-yl]amino}-4-(5-methylpyridin-3-yl)-1-{[2-(trimethylsilyl)ethoxy]methyl}-1H-pyrrolo[2,3-b]pyridine-3-carbonitrile (190 mg, 41%) as a pale yellow solid; LC-MS (Method C) (m/z) 528 [M+H]$^+$; tR=2.60.

The following intermediates of the invention were prepared analogously:

6-[(4-Chloro-1-methyl-1H-pyrazol-3-yl)amino]-4-(4-methylpyridin-2-yl)-1-{[2-(trimethylsilyl)ethoxy]methyl}-1H-pyrrolo[2,3-b]pyridine-3-carbonitrile

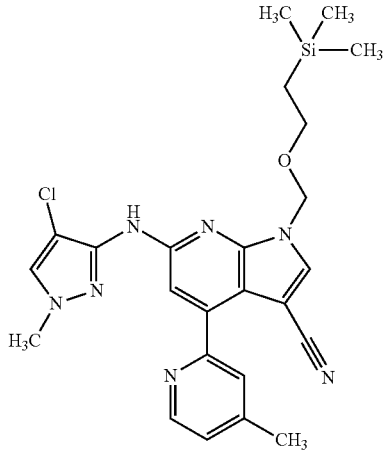 [SMILES: Cc1ccnc(-c2cc(Nc3nn(C)cc3Cl)nc3c2c(C#N)cn3COCC[Si](C)(C)C)c1]

280 mg obtained from 6-chloro-4-(4-methylpyridin-2-yl)-1-{[2-(trimethylsilyl)ethoxy]methyl}-1H-pyrrolo[2,3-b]pyridine-3-carbonitrile and 4-chloro-1-methyl-1H-pyrazol-3-amine in 45% yield as an off-white solid; LC-MS (Method C) (m/z) 494 [M+H]$^+$; tR=2.71.

6-[(1,4-Dimethyl-1H-pyrazol-3-yl)amino]-4-(6-methylpyridin-2-yl)-1-{[2-(trimethylsilyl)ethoxy]methyl}-1H-pyrrolo[2,3-b]pyridine-3-carbonitrile

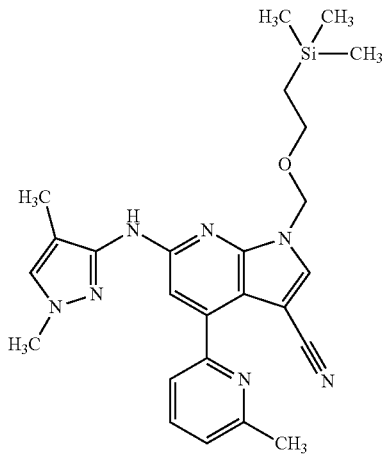 [SMILES: Cc1cccc(-c2cc(Nc3nn(C)cc3C)nc3c2c(C#N)cn3COCC[Si](C)(C)C)n1]

200 mg was obtained from 6-chloro-4-(6-methylpyridin-2-yl)-1-{[2-(trimethylsilyl)ethoxy]methyl}-1H-pyrrolo[2,3-b]pyridine-3-carbonitrile and 1,4-dimethyl-1H-pyrazol-3-amine in 67% yield; LC-MS (Method C) (m/z) 474 [M+H]$^+$; tR=2.55.

6-{[1-Methyl-4-(trifluoromethyl)-1H-pyrazol-3-yl]amino}-4-(6-methylpyridin-2-yl)-1-{[2-(trimethylsilyl)ethoxy]methyl}-1H-pyrrolo[2,3-b]pyridine-3-carbonitrile

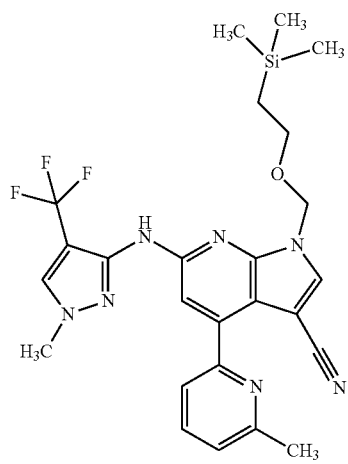 [SMILES: Cc1cccc(-c2cc(Nc3nn(C)cc3C(F)(F)F)nc3c2c(C#N)cn3COCC[Si](C)(C)C)n1]

190 mg was obtained from 6-chloro-4-(6-methylpyridin-2-yl)-1-{[2-(trimethylsilyl)ethoxy]methyl}-1H-pyrrolo[2,3-b]pyridine-3-carbonitrile and 1-methyl-4-(trifluoromethyl)-1H-pyrazol-3-amine in 48% yield; LC-MS (Method C) (m/z) 528 [M+H]$^+$; tR=2.93.

6-[(1-Methyl-1H-pyrazol-3-yl)amino]-4-(5-methylpyridin-3-yl)-1-{[2-(trimethylsilyl)ethoxy]methyl}-1H-pyrrolo[2,3-b]pyridine-3-carbonitrile

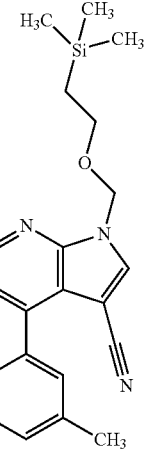

170 mg obtained from 6-chloro-4-(5-methylpyridin-3-yl)-1-{[2-(trimethylsilyl)ethoxy]methyl}-1H-pyrrolo[2,3-b]pyridine-3-carbonitrile and 1-methyl-1H-pyrazol-3-amine in 43% yield; LC-MS (Method C) (m/z) 460 [M+H]$^+$; tR=2.32.

6-[(1,4-Dimethyl-1H-pyrazol-3-yl)amino]-4-(2-methylpyridin-4-yl)-1-{[2-(trimethylsilyl)ethoxy]methyl}-1H-pyrrolo[2,3-b]pyridine-3-carbonitrile

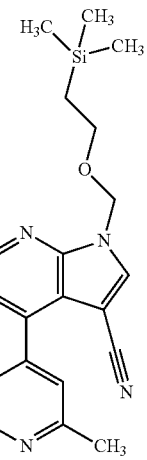

230 mg obtained from 6-chloro-4-(2-methylpyridin-4-yl)-1-{[2-(trimethylsilyl)ethoxy]methyl}-1H-pyrrolo[2,3-b]pyridine-3-carbonitrile and 1,4-dimethyl-1H-pyrazol-3-amine in 65% yield; LC-MS (Method C) (m/z) 474 [M+H]$^+$; tR=2.18.

Preparation of the Compounds of the Invention

Example 1

4-(3-Methoxyphenyl)-1H-pyrrolo[2,3-b]pyridine-3-carbonitrile

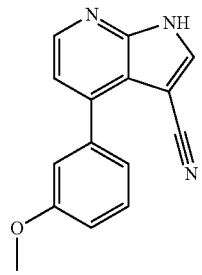 [SMILES: COc1cccc(-c2ccnc3[nH]cc(C#N)c23)c1]

A mixture of 4-chloro-1H-pyrrolo[2,3-b]pyridine-3-carbonitrile (0.1 g, 0.56 mmol), 3-methoxyphenylboronic acid (0.094 g, 0.62 mmol), potassium fluoride (0.098 g, 1.6.9 mmol), bis(tri-tert-butylphosphine)palladium(0) (0.003 g, 0.006 mmol), 1,4-dioxane (6 mL) and water (1 mL) was stirred at room temperature for 5 min under a stream of nitrogen. The stirred reaction mixture was then heated with microwaves at 150° C. for 30 min and cooled to room temperature. The reaction mixture was then partitioned between ethyl acetate (50 mL) and water (50 mL). The organic phase was separated, washed with water (2×20 mL), followed by brine (20 mL), dried (MgSO$_4$) and evaporated under reduced pressure. The residue was triturated with dichloromethane, and the residue was dried in vacuo to afford a light yellow solid (0.061 g, 44%), identified as 4-(3-methoxyphenyl)-1H-pyrrolo[2,3-b]pyridine-3-carbonitrile. LC-MS (Method B) (m/z) 250 (MH+); tR=1.14. $^1$H NMR (DMSO-d$_6$, 400 MHz) δ: 12.98 (1H, s, br), 8.52 (1H, s), 8.44-8.43 (1H, d), 7.46-7.42 (1H, m), 7.28-7.27 (1H, d), 7.19-7.16 (2H, m), 7.07-7.04 (1H, m), 3.85 (3H, s).

The following examples 2-5 were prepared analogously:

Example 2

4-(3-Methylphenyl)-1H-pyrrolo[2,3-b]pyridine-3-carbonitrile

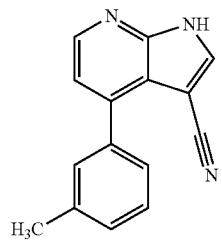 [SMILES: Cc1cccc(-c2ccnc3[nH]cc(C#N)c23)c1]

0.10 g prepared from 4-chloro-1H-pyrrolo[2,3-b]pyridine-3-carbonitrile (0.20 g, 1.13 mmol) and 3-methylphenylboronic acid (0.17 g, 1.24 mmol) as an off-white solid in 38% yield. LC-MS (Method A) (m/z) 234 (MH+); tR=2.18. $^1$H NMR (DMSO-d$_6$, 400 MHz) δ: 13.05 (1H, s, br), 8.50 (1H, s), 8.43-8.42 (1H, d), 7.46-7.44 (1H, m), 7.43-7.40 (2H, m), 7.34-7.29 (1H, m), 7.25-7.24 (1H, d), 2.40 (3H, s).

Example 3

4-(3-Ethylphenyl)-1H-pyrrolo[2,3-b]pyridine-3-carbonitrile

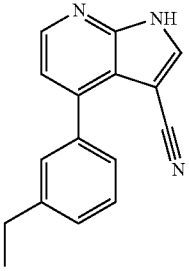 [SMILES: CCc1cccc(-c2ccnc3[nH]cc(C#N)c23)c1]

0.065 g prepared from 4-chloro-1H-pyrrolo[2,3-b]pyridine-3-carbonitrile (0.10 g, 0.56 mmol) and 3-ethylphenylboronic acid (0.09 g, 0.62 mmol) as an off-white solid in 47% yield. LC-MS (Method A) (m/z) 248 (MH+); tR=2.37. $^1$H NMR (DMSO-d$_6$, 400 MHz) δ: 12.96 (1H, s, br), 8.51 (1H, s), 8.44-8.42 (1H, d), 7.48-7.41 (3H, m), 7.36-7.33 (1H, m), 7.25-7.24 (1H, d), 2.73-2.67 (2H, q), 1.27-1.24 (3H, t).

Example 4

4-(Thiophen-3-yl)-1H-pyrrolo[2,3-b]pyridine-3-carbonitrile

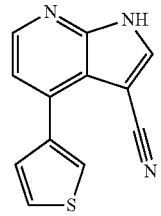 [SMILES: N#Cc1c[nH]c2nccc(-c3ccsc3)c12]

0.023 g prepared from 4-chloro-1H-pyrrolo[2,3-b]pyridine-3-carbonitrile (0.10 g, 0.56 mmol) and thiophene-3-boronic acid as a yellow solid in 18% yield. LC-MS (Method A) (m/z) 226 (MH+); tR=2.09. $^1$H NMR (DMSO-d$_6$, 400 MHz) δ: 12.94 (1H, s, br), 8.51 (1H, s, br), 8.41-8.40 (1H, d), 7.93-7.92 (1H, dd), 7.75-7.73 (1H, dd), 7.48-7.47 (1H, dd), 7.30-7.29 (1H, d).

Example 5

4-[4-(Morpholin-4-ylmethyl)phenyl]-1H-pyrrolo[2,3-b]pyridine-3-carbonitrile

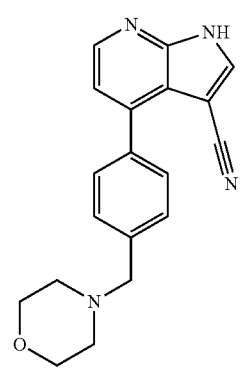 [SMILES: N#Cc1c[nH]c2nccc(-c3ccc(CN4CCOCC4)cc3)c12]

0.078 g prepared from 4-chloro-1H-pyrrolo[2,3-b]pyridine-3-carbonitrile (0.10 g, 0.56 mmol) and 4-(4-morpholinomethyl)phenylboronic acid pinacol ester hydrochloride (0.21 g, 0.62 mmol) as an off-white solid in 44% yield. LC-MS (Method A) (m/z) 319 (MH+); tR=1.54. $^1$H NMR (DMSO-$d_6$, 400 MHz) δ: 12.96 (1H, s, br), 8.51 (1H, s), 8.44-8.43 (1H, d), 7.59-7.57 (2H, d), 7.47-7.45 (2H, d), 7.25-7.24 (1H, d), 3.61-3.58 (4H, m), 3.56 (2H, s), 2.42-2.38 (4H, m).

Example 6

4-[1-(Morpholin-4-ylmethyl)pyrrol-3-yl]-1H-pyrrolo[2,3-b]pyridine-3-carbonitrile

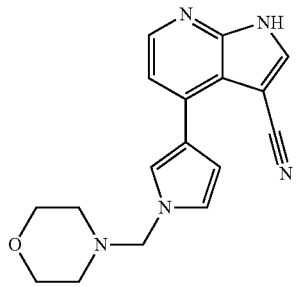 [SMILES: N#Cc1c[nH]c2nccc(-c3ccn(CN4CCOCC4)c3)c12]

1-(Benzenesulfonyl)-4-[1-(morpholin-4-ylmethyl) pyrrol-3-yl]pyrrolo[2,3-b]pyridine-3-carbonitrile (0.029 g) was taken up in tetrahydrofuran (4 mL). Water (1 mL) and potassium carbonate (0.041 g) were added and the reaction mixture was heated to 120° C. for 30 minutes in a sealed microwave process vial. The cooled reaction mixture was then partitioned between ethyl acetate (50 mL) and brine (30 mL). The separated organic phase was then dried over magnesium sulphate and concentrated in vacuo. The residue was then loaded onto a 10 g silica column, and eluted on a gradient using dichloromethane and methanol/dichloromethane (2.5:97.5). The eluted material, obtained as a white solid (0.005 g, 26%), was identified as 4-[1-(morpholin-4-ylmethyl)pyrrol-3-yl]-1H-pyrrolo[2,3-b]pyridine-3-carbonitrile. LC-MS (Method A) (m/z) 308 (MH$^+$); $t_R$=1.86. $^1$H NMR (DMSO-$d_6$, 400 MHz) δ: 12.77 (1H, s, br), 8.44 (1H, s), 8.29-8.28 (1H, d), 7.40-7.39 (1H, dd), 7.24-7.22 (1H, d), 6.95-6.94 (1H, dd), 6.59-6.58 (1H, dd), 4.75 (2H, s), 3.59-3.55 (4H, m).

Example 7

4-[3-Methyl-4-(morpholin-4-ylmethyl)phenyl]-1H-pyrrolo[2,3-b]pyridine-3-carbonitrile

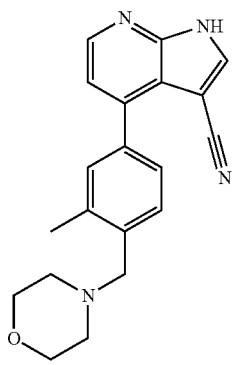 [SMILES: Cc1cc(-c2ccnc3[nH]cc(C#N)c23)ccc1CN1CCOCC1]

The title compound was prepared by analogy with Example 7 (using potassium carbonate in methanol) from 1-(benzenesulfonyl)-4-[3-methyl-4-(morpholin-4-ylmethyl)phenyl]-1H-pyrollo[2,3-b]pyridine-3-carbonitrile to furnish a white solid. Yield: 108 mg, 39%.

LC-MS (m/z) (Method A) 333 (MH$^+$); $t_R$=1.73. $^1$H NMR (DMSO-$d_6$, 400 MHz) δ: 12.95 (1H, s, br), 8.51 (1H, s), 8.44-8.42 (1H, d), 7.45 (1H, s), 7.41-7.39 (2H, d), 7.26-7.25 (1H, d), 3.60-3.56 (4H, m), 3.52 (2H, s), 2.43-2.39 (7H, m).

Example 8

4-{4-[(Dimethylamino)methyl]-3-methylphenyl}-1H-pyrrolo[2,3-b]pyridine-3-carbonitrile

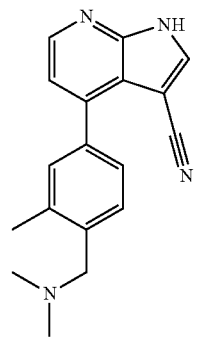 [SMILES: Cc1cc(-c2ccnc3[nH]cc(C#N)c23)ccc1CN(C)C]

The title compound was prepared analogously from Suzuki coupling with 1-(benzenesulfonyl)-4-chloro-1H-pyrrolo[2,3-b]pyridine-3-carbonitrile and 4-formyl-3-methylphenylboronic acid, followed by reductive amination with dimethylamine and de-protection with aqueous potassium carbonate (as per Example 7) to furnish a white solid. Yield: 36 mg, 53%.

LC-MS (Method A) (m/z) 291 (MH$^+$); $t_R$=1.7. $^1$H NMR (DMSO-$d_6$, 400 MHz) δ: 12.95 (1H, s, br), 8.51 (1H, s), 8.44-8.42 (1H, d), 7.44-7.35 (3H, m), 7.27-7.26 (1H, d), 3.43 (2H, s), 2.41 (3H, s), 2.20 (6H, s).

Example 9

4-[3-Ethyl-4-(morpholin-4-ylmethyl)phenyl]-1H-pyrrolo[2,3-b]pyridine-3-carbonitrile

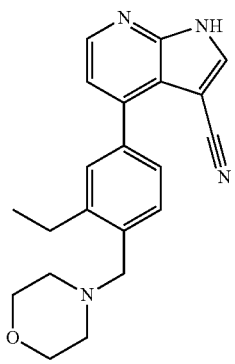 [SMILES: CCc1cc(-c2ccnc3[nH]cc(C#N)c23)ccc1CN1CCOCC1]

4-[3-Ethenyl-4-(morpholin-4-ylmethyl)phenyl]-1H-pyrollo[2,3-b]pyridine-3-carbonitrile (0.032 g) was taken up in methanol (10 mL) and then 10% palladium on carbon (catalytic amount) was added. The reaction mixture was degassed with nitrogen and then shaken under hydrogen (ambient pressure). After 2.5 hours, the reaction mixture was filtered through a pad of Celite, which was then washed with further methanol. The eluent was concentrated in vacuo, and the residue subjected silica gel column chromatography. Gradient elution with dichloromethane then ethyl acetate/dichloromethane (1:1) afforded a white solid (0.012 g, 38%), identified as 4-[3-ethyl-4-(morpholin-4-ylmethyl)phenyl]-1H-pyrrolo[2,3-b]pyridine-3-carbonitrile. LC-MS (Method A) (m/z) 347 (MH$^+$); $t_R$=1.82. $^1$H NMR (DMSO-d$_6$, 400 MHz) δ: 12.95 (1H, s, br), 8.51 (1H, s), 8.44-8.43 (1H, d), 7.47-7.38 (3H, m), 7.27-7.25 (1H, d), 3.60-3.56 (4H, m), 3.55 (2H, s), 2.81-2.76 (2H, q), 2.43-2.38 (4H, m), 1.28-1.24 (3H, t).

Example 10

4-[3-Methoxy-4-(morpholin-4-ylmethyl)phenyl]-1H-pyrrolo[2,3-b]pyridine-3-carbonitrile

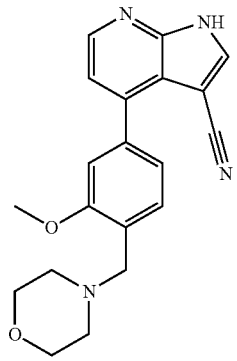 [SMILES: COc1cc(-c2ccnc3[nH]cc(C#N)c23)ccc1CN1CCOCC1]

The title compound was prepared by analogy with Example 7 via Suzuki coupling with 1-(benzenesulfonyl)-4-chloro-1H-pyrollo[2,3-b]pyridine-3-carbonitrile and 2-methoxy-4-(tetramethyl-1,3,2-dioxaborolan-2-yl)benzaldehyde (Colombo et at, Org. Lett, 2007, 9, 21, 4319-4322), followed by reductive amination with morpholine and deprotection with aqueous potassium carbonate. Yield: 0.029 g, 26%. LC-MS (Method A) (m/z) 349 (MH$^+$); $t_R$=1.73. $^1$H NMR (DMSO-d$_6$, 400 MHz) δ: 12.95 (1H, s, br), 8.53 (1H, s), 8.45-8.44 (1H, d), 7.49-7.47 (1H, d), 7.31-7.29 (1H, d), 7.24 (1H, s), 7.19-7.17 (1H, d), 3.91 (3H, s), 3.64-3.56 (4H, m), 3.55 (2H, s), 2.46-2.39 (4H, m).

Example 11

6-Amino-4-phenyl-1H-pyrrolo[2,3-b]pyridine-3-carbonitrile

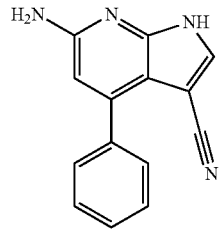 [SMILES: N#Cc1c[nH]c2nc(N)cc(-c3ccccc3)c12]

6-Amino-4-chloro-1H-pyrrolo[2,3-b]pyridine-3-carbonitrile (0.047 g), phenylboronic acid (0.060 g), potassium fluoride (0.043 g), bis(tri-tert-butylphosphine)palladium(0) (0.006 g) were suspended in 1,4-dioxane:water (6:1, 3.5 mL). The reaction mixture was then stirred at room temperature and degased with nitrogen for 5 min. The reaction mixture was then heated to 120° C. for 60 minutes in a sealed microwave process vial. After cooling to room temperature, the reaction mixture was diluted with ethyl acetate (20 mL) and water (20 mL), and filtered through Celite. The ethyl acetate layer was separated and the aqueous layer was extracted with ethyl acetate (3×20 mL). The combined organic phases were washed with brine (20 mL), dried over magnesium sulfate and concentrated in vacuo. The residue was purified by silica-gel flash chromatography [ethyl acetate-isohexane (0-100%), gradient elution]. The eluted material, obtained as a beige solid (0.033 g, 58%) was identified as 6-amino-4-phenyl-1H-pyrrolo[2,3-b]pyridine-3-carbonitrile. LC-MS (Method A) (m/z) 235 (MH+); tR=1.96. $^1$H NMR (DMSO-d$_6$, 400 MHz) δ: 12.09 (1H, s, br), 7.93 (1H, s), 7.55-7.43 (5H, m), 6.37 (1H, s), 6.09 (2H, s, br).

Example 12

6-Amino-4-(3-methylphenyl)-1H-pyrrolo[2,3-b]pyridine-3-carbonitrile

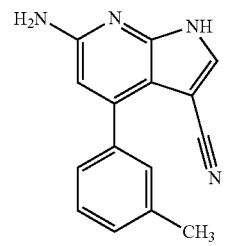 [SMILES: Cc1cccc(-c2cc(N)nc3[nH]cc(C#N)c23)c1]

6-(Benzylamino)-4-(3-methylphenyl-1H-pyrrolo[2,3-b]pyridine-3-carbonitrile (0.063 g) was dissolved in ethanol (5 mL). 10% palladium on carbon (~15% of starting material in weight) was added, and the reaction mixture was shaken under hydrogen (ambient pressure) overnight. LC-MS showed that largely starting material remained. The solvent was removed under reduced pressure, and then acetic acid (10 mL) was added followed by fresh 10% palladium on carbon (one spatula-full). The mixture was shaken under hydrogen (ambient pressure) overnight. Reaction mixture was then filtered through Celite, washed with ethyl acetate, and then evaporated to a brown gum (0.039 g, 84%), identified as 6-amino-4-(3-methylphenyl)-1H-pyrrolo[2,3-b]pyridine-3-carbonitrile. LC-MS (Method A) (m/z) 249 (MH+); tR=2.17. $^1$H NMR (DMSO-d$_6$, 400 MHz) δ: 12.10 (1H, s, br), 7.93 (1H, s), 7.39-7.35 (2H, m), 7.33-7.30 (1H, m), 7.28-7.25 (1H, m), 6.38 (1H, s), 6.08 (2H, s, br), 2.38 (3H, s).

Example 13

6-[1-(1-Methylpyrazol-3-yl)amino]-4-phenyl-1H-pyrrolo[2,3-b]pyridine-3-carbonitrile

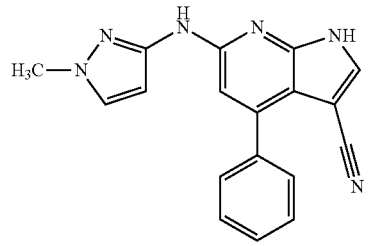 [SMILES: Cn1ccc(Nc2cc(-c3ccccc3)c3c(C#N)c[nH]c3n2)n1]

4-Chloro-6-[(1-methyl-1H-pyrazol-3-yl)amino]-1H-pyrrolo[2,3-b]pyridine-3-carbonitrile (0.055 g), phenylboronic acid (0.049 g), potassium fluoride (0.035 g) and bis(tri-tert-butylphosphine)palladium(0) (0.005 g) were suspended in 1,4-dioxane:water (6:1, 3.5 mL). The reaction mixture was then stirred at room temperature under a stream of nitrogen for 5 min, and then heated to 120° C. with microwaves for 60 minutes in a sealed process vial. After cooling to room temperature, the reaction mixture was diluted with ethyl acetate (20 mL) and water (20 mL), and filtered through Celite. The organic phase was separated, and the aqueous layer was extracted with ethyl acetate (3×20 mL). The combined organic extracts were washed with brine (20 mL), dried over magnesium sulfate and concentrated in vacuo. The residue was subjected to silica-gel flash chromatography [ethyl acetate-isohexane (0-100%)]. The eluted material, obtained as a beige solid 0.025 g (39%), was identified as 6-[(1-methylpyrazol-3-yl)amino]-4-phenyl-1H-pyrrolo[2,3-b]pyridine-3-carbonitrile. LC-MS (Method A) (m/z) 315 (MH+); tR=2.24. $^1$H NMR (DMSO-$d_6$, 400 MHz) δ: 12.31-12.30 (1H, d, br), 9.46 (1H, s), 8.06-8.05 (1H, d), 7.57-7.46 (6H, m), 6.93 (1H, s), 6.64 (1H, d), 3.74 (3H, s).

Example 14

4-(3-Methylphenyl)-6-[(1-methylpyrazol-3-yl)amino]-1H-pyrrolo[2,3-b]pyridine-3-carbonitrile

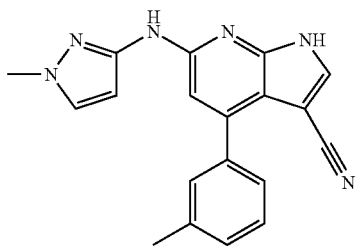 [SMILES: Cc1cccc(-c2cc(Nc3ccn(C)n3)nc3[nH]cc(C#N)c23)c1]

4-Chloro-6-[(1-methyl-1H-pyrazol-3-yl)amino]-1H-pyrrolo[2,3-b]pyridine-3-carbonitrile (0.085 g), 3-methylphenylboronic acid (0.085 g), potassium fluoride (0.054 g), bis(tri-tert-butylphosphine)palladium(0) (0.008 g) were suspended in 1,4-dioxane:water (6:1, 3.5 mL) and stirred at room temperature under a stream of nitrogen. The reaction mixture was then heated with microwaves at 120° C. for 60 minutes in a sealed process vial. After cooling to room temperature, the reaction mixture was diluted with ethyl acetate (20 mL) and water (20 mL), and filtered through Celite. The organic phase was extracted and the aqueous layer was extracted with ethyl acetate (3×20 mL). The combined organic extracts were washed with brine (20 mL), dried over magnesium sulfate and concentrated in vacuo. The residue was subjected to silica-gel flash column chromatography [ethyl acetate-isohexane (0-100%), gradient elution]. The eluted material, obtained as an off-white solid (0.028 g, 27%), was identified as 4-(3-methylphenyl)-6-[(1-methylpyrazol-3-yl)amino]-1H-pyrrolo[2,3-b]pyridine-3-carbonitrile. LC-MS (m/z) (Method B) 329 (MH+); tR=1.16. $^1$H NMR (DMSO-$d_6$, 400 MHz) δ: 12.28 (1H, s, br), 9.44 (1H, s), 8.05-8.04 (1H, d), 7.55-7.54 (1H, d), 7.42-7.38 (2H, m), 7.35-7.32 (1H, m), 7.30-7.27 (1H, m), 6.93 (1H, s), 6.65-6.64 (1H, d), 3.74 (3H, s), 2.39 (3H, s).

Example 15

4-[3-Methyl-4-(morpholin-4-ylmethyl)phenyl]-6-[(1-methylpyrazol-3-yl)amino]-1H-pyrrolo[2,3-b]pyridine-3-carbonitrile

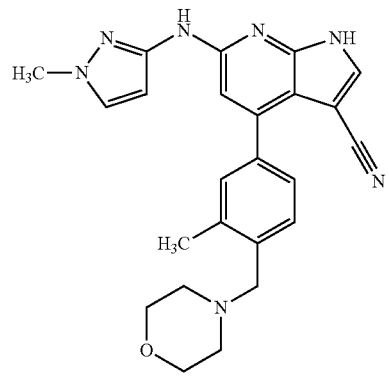 [SMILES: Cc1cc(-c2cc(Nc3ccn(C)n3)nc3[nH]cc(C#N)c23)ccc1CN1CCOCC1]

4-(4-Formyl-3-methylphenyl)-6-[(1-methylpyrazol-3-yl)amino]-1H-pyrrolo[2,3-b]pyridine-3-carbonitrile (0.014 g) and morpholine (0.017 g) were dissolved in dichloroethane (5 mL). Two drops of acetic acid were then added, followed by sodium triacetoxy borohydride. The reaction mixture was stirred at room temperature for 16 h. The solvent was then removed under reduced pressure, and the residue subjected to silica-gel flash column chromatography [dichloromethane-methanol (0-10%), gradient elution]. The eluted material, obtained as a yellow solid (0.003 g, 18%), was identified as 4-[3-methyl-4-(morpholin-4-ylmethyl)phenyl]-6-[(1-methylpyrazol-3-yl)amino]-1H-pyrrolo[2,3-b]pyridine-3-carbonitrile. LC-MS (m/z) (Method B) 426 (M–H+); tR=0.88. $^1$H NMR (DMSO-$d_6$, 400 MHz) δ: 12.24 (1H, s, br), 9.43 (1H, s), 8.04 (1H, s), 7.55-7.54 (1H, d), 7.38-7.31 (3H, m), 6.92 (1H, s), 6.65-6.64 (1H, d), 3.74 (3H, s), 3.60-3.57 (4H, m), 3.50 (2H, s), 2.43-2.39 (7H, m).

Example 16

6-[(1-Methylpyrazol-4-yl)amino]-4-phenyl-1H-pyrrolo[2,3-b]pyridine-3-carbonitrile

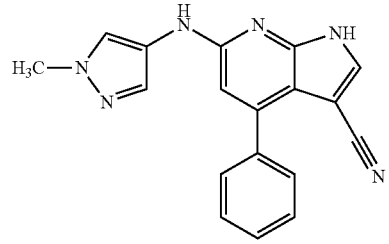 [SMILES: Cn1cc(Nc2cc(-c3ccccc3)c3c(C#N)c[nH]c3n2)cn1]

4-Chloro-6-[(1-methyl-1H-pyrazol-4-yl)amino]-1H-pyrrolo[2,3-b]pyridine-3-carbonitrile (0.054 g), phenylboronic acid (0.027 g), potassium fluoride (0.035 g) and bis(tri-tert-butylphosphine)palladium(0) (0.00123 g) were suspended in 1,4-dioxane-water (6:1, 3.5 mL). The reaction mixture was stirred at room temperature under a stream of nitrogen for 5 min, and then heated to 120° C. with microwaves for 60 minutes in a sealed process vial. After cooling to room temperature, the reaction mixture was diluted with ethyl acetate (20 mL) and water (20 mL), and filtered through Celite. The organic phase was separated, and the aqueous layer was extracted with ethyl acetate (3×20 mL). The combined organic extracts were washed with brine (20 mL), dried over magnesium sulfate and concentrated in vacuo. The residue was subjected to silica-gel flash column chromatography [ethyl acetate-isohexane (0-100%), gradient elution]. The eluted material, obtained as a beige solid (0.045 g, 72%), was identified as 6-[(1-methylpyrazol-4-yl)amino]-4-phenyl-1H-pyrrolo[2,3-b]pyridine-3-carbonitrile. LC-MS (Method A) (m/z) 315 (M+H+); tR=1.76. ¹H NMR (DMSO-d₆, 400 MHz) δ: 12.29-12.28 (1H, d, br), 9.02 (1H, s), 8.02-8.01 (2H, m), 7.58-7.45 (6H, m), 6.55 (1H, s), 3.83 (3H, s).

Example 17

4-Phenyl-6-(pyridin-2-ylamino)-1H-pyrrolo[2,3-b]pyridine-3-carbonitrile

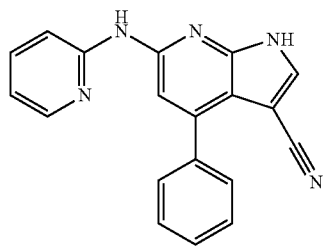 [SMILES: N#Cc1c[nH]c2nc(Nc3ccccn3)cc(-c3ccccc3)c12]

4-Chloro-6-[(pyridin-2-yl)amino]-1H-pyrrolo[2,3-b]pyridine-3-carbonitrile (0.125 g), phenylboronic acid (0.113 g), potassium fluoride (0.081 g) and bis(tri-tert-butylphosphine)palladium(0) (0.012 g) were suspended in 1,4-dioxane-water (6:1, 3.5 mL) and stirred at room temperature under a stream of nitrogen for 5 min. The reaction mixture was then heated to 120° C. with microwaves for 60 minutes in a sealed process vial. After cooling to room temperature, the reaction mixture was diluted with ethyl acetate (20 mL) and water (20 mL), and filtered through Celite. The organic phase was separated and the aqueous layer was extracted with ethyl acetate (3×20 mL). The combined organic extracts were washed with brine (20 mL), dried over magnesium sulfate and concentrated in vacuo. The residue was subjected to silica-gel flash column chromatography [ethyl acetate-isohexane (0-50%), gradient elution]. The eluted material, obtained as an off-white solid (0.018 g, 13%), was identified as 4-phenyl-6-(pyridin-2-ylamino)-1H-pyrrolo[2,3-b]pyridine-3-carbonitrile. LC-MS (Method A) (m/z) 312 (M+H+); tR=1.39. ¹H NMR (DMSO-d₆, 400 MHz) δ: 12.55 (1H, s, br), 9.85 (1H, s), 8.25-8.23 (1H, m), 8.19 (1H, s), 8.15-8.13 (1H, m), 7.73-7.69 (1H, m), 7.61-7.48 (5H, m), 7.40 (1H, s), 6.92-6.88 (1H, m).

Example 18

6-{[1-Methyl-4-(trifluoromethyl)-1H-pyrazol-3-yl]amino}-4-(5-methylpyridin-3-yl)-1H-pyrrolo[2,3-b]pyridine-3-carbonitrile

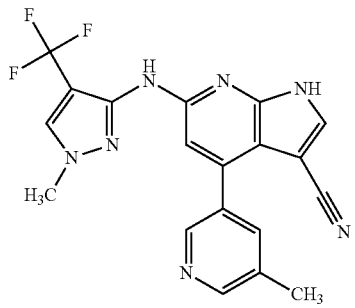 [SMILES: Cc1cncc(-c2cc(Nc3nn(C)cc3C(F)(F)F)nc3[nH]cc(C#N)c23)c1]

To a solution of 6-{[1-methyl-4-(trifluoromethyl)-1H-pyrazol-3-yl]amino}-4-(5-methylpyridin-3-yl)-1-{[2-(trimethylsilyl)ethoxy]methyl}-1H-pyrrolo[2,3-b]pyridine-3-carbonitrile (190 mg, 0.36 mmol) in tetrahydrofuran (10.0 mL) was added triethylamine (3.0 mL) and tetra-n-butylammonium fluoride (1.0 M in tetrahydrofuran, 1.8 mL, 1.80 mmol) at ambient temperature. The reaction mixture was then heated to 75° C. and stirred for 18 h. On completion of the reaction (monitored by TLC), water was added and the reaction mixture was extracted with ethyl acetate (3×30 mL). The combined organic layers were dried over anhydrous sodium sulfate and evaporated under reduced pressure. The residue was subjected to silica-gel (100-200 mesh) column chromatography, eluted with 2% methanol in dichloromethane, to afford 6-{[1-methyl-4-(trifluoromethyl)-1H-pyrazol-3-yl]amino}-4-(5-methylpyridin-3-yl)-1H-pyrrolo[2,3-b]pyridine-3-carbonitrile (100 mg, 37%) as a pale yellow solid. LC-MS (Method D) (m/z) 398 [M+H]⁺; tR=1.63 min. ¹H NMR (DMSO-d₆, 400 MHz) δ: 12.41 (1H, br, s), 8.68 (1H, s), 8.55-8.52 (2H, m), 8.27 (1H, s), 8.08 (1H, s), 7.82 (1H, s), 6.79 (1H, s), 3.83 (3H, s), 2.39 (3H, s).

The following examples 19-23 were prepared analogously:

Example 19

6-[(4-Chloro-1-methyl-1H-pyrazol-3-yl)amino]-4-(4-methylpyridin-2-yl)-1H-pyrrolo[2,3-b]pyridine-3-carbonitrile

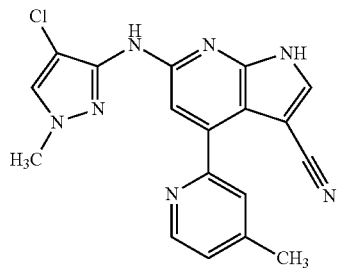 [SMILES: Cc1ccnc(-c2cc(Nc3nn(C)cc3Cl)nc3[nH]cc(C#N)c23)c1]

46 mg prepared from 6-[(4-chloro-1-methyl-1H-pyrazol-3-yl)amino]-4-(4-methylpyridin-2-yl)-1-{[2-(trimethylsilyl)ethoxy]methyl}-1H-pyrrolo[2,3-b]pyridine-3-carbonitrile as a pale yellow solid in 37% yield; LC-MS (Method D) (m/z) 364 [M+H]⁺; tR=1.84. ¹H NMR (DMSO-d₆, 400 MHz) δ: 12.35 (1H, s), 8.62 (1H, s), 8.58-8.56 (1H, d, J=4.8 Hz), 8.05-8.04 (1H, d, J=2.8 Hz), 7.90 (1H, s), 7.58 (1H, s), 7.31-7.30 (1H, d, J=4.8 Hz), 6.98 (1H, s), 3.78 (3H, s), 2.41 (3H, s).

Example 20

6-[(1,4-Dimethyl-1H-pyrazol-3-yl)amino]-4-(6-methylpyridin-2-yl)-1H-pyrrolo[2,3-b]pyridine-3-carbonitrile

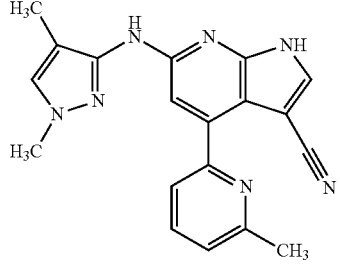 [SMILES: Cc1cccc(-c2cc(Nc3nn(C)cc3C)nc3[nH]cc(C#N)c23)n1]

46 mg from 6-[(1,4-dimethyl-1H-pyrazol-3-yl)amino]-4-(6-methylpyridin-2-yl)-1-{[2-(trimethylsilyl)ethoxy]methyl}-1H-pyrrolo[2,3-b]pyridine-3-carbonitrile as a pale yellow solid in 32% yield; LC-MS (Method D) (m/z) 344 [M+H]$^+$; tR=1.78. $^1$H NMR (DMSO-d$_6$, 400 MHz) δ: 12.21 (1H, s), 8.49 (1H, s), 8.00 (1H, s), 7.85-7.81 (1H, t, J=7.6 Hz), 7.51-7.49 (1H, d, J=7.6 Hz), 7.40 (1H, s), 7.33-7.31 (1H, d, J=7.6 Hz), 7.02 (1H, s), 3.71 (3H, s), 2.58 (3H, s), 1.88 (3H, s).

Example 21

6-{[1-Methyl-4-(trifluoromethyl)-1H-pyrazol-3-yl]amino}-4-(6-methylpyridin-2-yl)-1H-pyrrolo[2,3-b]pyridine-3-carbonitrile

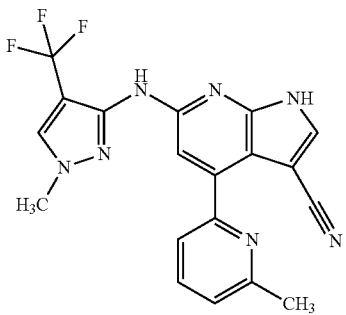 [SMILES: Cc1cccc(-c2cc(Nc3nn(C)cc3C(F)(F)F)nc3[nH]cc(C#N)c23)n1]

47 mg from 6-{[1-methyl-4-(trifluoromethyl)-1H-pyrazol-3-yl]amino}-4-(6-methylpyridin-2-yl)-1-{[2-(trimethylsilyl)ethoxy]methyl}-1H-pyrrolo[2,3-b]pyridine-3-carbonitrile in 33% yield as an off-white solid; LC-MS (Method C) (m/z) 398 [M+H]$^+$; tR=1.79. $^1$H NMR (DMSO-d$_6$, 400 MHz) δ: 12.35 (1H, s), 8.67 (1H, s), 8.27 (1H, s), 8.05-8.04 (1H, d, J=4.0 Hz), 7.87-7.82 (1H, m), 7.54-7.51 (1H, d, J=10.4 Hz), 7.35-7.327 (1H, d, J=10.4 Hz), 7.00 (1H, s), 3.84 (3H, s), 2.58 (3H, s).

Example 22

6-[(1-Methyl-1H-pyrazol-3-yl)amino]-4-(5-methylpyridin-3-yl)-1H-pyrrolo[2,3-b]pyridine-3-carbonitrile

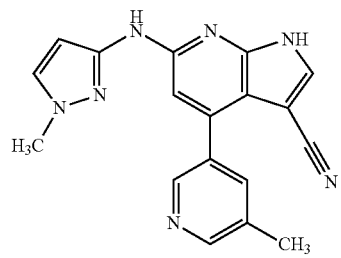 [SMILES: Cc1cncc(-c2cc(Nc3ccn(C)n3)nc3[nH]cc(C#N)c23)c1]

22 mg from 6-[(1-methyl-1H-pyrazol-3-yl)amino]-4-(5-methylpyridin-3-yl)-1-{[2-(trimethylsilyl)ethoxy]methyl}-1H-pyrrolo[2,3-b]pyridine-3-carbonitrile in 18% yield as an off white solid; LC-MS (Method D) (m/z) 330 [M+H]$^+$; tR=1.51. $^1$H NMR (DMSO-d$_6$, 400 MHz) δ: 12.34 (1H, s), 9.47 (1H, s), 8.55-8.52 (2H, m), 8.08-8.07 (1H, d, J=2.8 Hz), 7.82 (1H, s), 7.555-7.550 (1H, d, J=2.0 Hz), 6.96 (1H, s), 6.64-6.63 (1H, d, J=2.4 Hz), 3.74 (3H, s), 2.39 (3H, s).

Example 23

6-[(1,4-Dimethyl-1H-pyrazol-3-yl)amino]-4-(2-methylpyridin-4-yl)-1H-pyrrolo[2,3-b]pyridine-3-carbonitrile

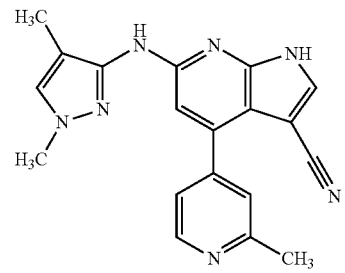 [SMILES: Cc1cc(-c2cc(Nc3nn(C)cc3C)nc3[nH]cc(C#N)c23)ccn1]

35 mg from 6-[(1,4-dimethyl-1H-pyrazol-3-yl)amino]-4-(2-methylpyridin-4-yl)-1-{[2-(trimethylsilyl)ethoxy]methyl}-1H-pyrrolo[2,3-b]pyridine-3-carbonitrile as a yellow solid in 21% yield; LC-MS (Method D) (m/z) 344 [M+H]$^+$; tR=1.45. $^1$H NMR (DMSO-d$_6$, 400 MHz) δ: 12.34 (1H, s), 8.56 (2H, m), 8.05 (1H, s), 7.42 (1H, s), 7.40 (1H, s), 7.33-7.32 (1H, d, J=5.2 Hz), 6.82 (1H, s), 3.70 (3H, s), 2.55 (3H, s), 1.88 (3H, s).

LRRK2 Wild-Type and G2019S Kinase Activity Assay

LRRK2 kinase activity is measured using a LanthaScreen kinase activity assay available from Invitrogen (Life Technologies Corporation). The assay is a homogeneous time resolved-fluorescence resonance energy transfer (TR-FRET) assay that measures phosphorylation of a fluorescein-labelled peptide substrate (fluorescein-LRRKtide, fluorescein-GAGRLGRDKYKTLRQIRQ) (SEQ ID NO 1) as a result of LRRK2 kinase activity. The phosphorylated peptide is recognized by a terbium-labelled phospho-specific anti-LRRKtide antibody and, subsequently, the phosphorylated LRRKtide can be quantified by the extent of TR-FRET between the terbium donor and fluorescein acceptor.

The LRRK2 kinase is obtained from Invitrogen (Life Technologies Corporation) and comprises residues 970 to 2527 of the full length human wild-type LRRK2 kinase or a similar sequence with the G2019S mutation. As discussed above, this mutation increases the kinase activity relative to the wild-type. The kinase reactions are performed in a 20 µL volume in 384-well plates. The kinase reaction buffer consists of 50 mM Tris pH 8.5, 0.01% BRIJ-35, 10 mM MgCl$_2$, 1 mM EGTA, and 2 mM DTT.

In the assay, 1 nM LRRK2 WT or 250 pM LRRK2 G2019S kinase is incubated with the test compound (typically at 0 to 30 µM) for 30 minutes before the kinase reaction is initiated by addition of 1.3 mM ATP and 0.4 µM fluorescein-LRRKtide. The reaction mixture (20 µl total volume) is incubated for 2 hours at 30° C. before the reaction is terminated by addition of 10 mM EDTA and 1 nM terbium-labelled anti-phospho-LRRKtide antibody (final volume 20 µl). The mixture is further incubated for 30 minutes at RT. TR-FRET is measured by excitation of the terbium-donor with 340 nm light and subsequent (delay time 100 µs) measurement of terbium and fluorescein emission at 495 nm and 520 nm, respectively, over a time window of 1000 µs. The measurement is repeated 10 times for fluorescein and 10 times for terbium emission with a 2000 μs time window between repeats. TR-FRET measurements are performed on a Biomek Synergy plate. The TR-FRET signal is calculated as the emission-ratio at 520 nm over 495 nm.

The TR-FRET ratio readout for test compounds is normalized to 0% inhibition corresponding to TR-FRET ratio measured in control wells with no inhibition of the kinase activity and 100% inhibition corresponding to TR-FRET ratio measured in control wells with no kinase. Test compound potency ($IC_{50}$) was estimated by nonlinear regression using the sigmoidal dose-response (variable slope) using Xlfit 4 (IDBS, Guildford, Surrey, UK, model 205). $y=(A+((B-A)/(1+((C/x)^D))))$, where y is the normalized TR-TRET ratio measurement for a given concentration of test compound, x is the concentration of test compound, A is the estimated efficacy (% inhibition) at infinite compound dilution, and B is the maximal efficacy (% inhibition). C is the $IC_{50}$ value and D is the Hill slope coefficient. $IC_{50}$ estimates were obtained from independent experiment and the logarithmic average was calculated.

The table below shows the $IC_{50}$ values obtained as described above for the exemplified compounds.

| Example no: | LRRK2 G2019S $IC_{50}$ (nM) | LRRK2 WT $IC_{50}$ (nM) |
|---|---|---|
| 1 | 201 | 247 |
| 2 | 195 | 170 |
| 3 | 252 | 266 |
| 4 | 851 | 1279 |
| 5 | 1308 | 5442 |
| 6 | 650 | 3868 |
| 7 | 78 | 620 |
| 8 | 288 | 549 |
| 9 | 26 | 149 |
| 10 | 154 | 919 |
| 11 | 240 | 216 |
| 12 | 17 | 15 |
| 13 | 58 | 48 |
| 14 | 2 | 1 |
| 15 | 1 | 4 |
| 16 | 164 | 97 |
| 17 | 527 | 340 |
| 18 | 509 | 358 |
| 19 | 215 | 145 |
| 20 | 50 | 36 |
| 21 | 575 | 393 |
| 22 | 37 | 27 |
| 23 | 108 | 215 |

What is claimed is:

1. A method for the treatment of Lewy body dementia or Parkinson's disease comprising the administration of a therapeutically effective amount of a pharmaceutical composition comprising a compound according to Formula A, or a pharmaceutically acceptable salt of said compound, to a subject in need thereof, wherein said compound according to Formula A is:

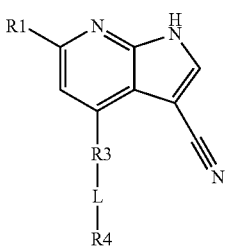

Formula A wherein
R1 represents a NHR2 group;
R2 represents H or a 5 or 6 membered heteroaromatic ring with 1 or 2 N, which heteroaromatic ring is optionally substituted with 1 or 2 groups each independently selected from the group consisting of: $CF_3$, halogen, $C_1$-$C_3$ alkyl, $C_1$-$C_3$ alkoxy, $C_1$-$C_3$ alkylamine and $C_1$-$C_3$ alkoxy amine;
R3 represents a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 $C_1$-$C_3$ alkyl, 1 or 2 $C_1$-$C_3$ alkoxy or a trifluoromethyl;
L is absent or represents $(CH_2)_n$, wherein n=1 or 2; and
R4 represents H, $NH_2$ or a 5 or 6 membered heterocyclic ring with 1 or 2 heteroatom(s) selected from N or O, which heterocyclic ring is optionally substituted with 1 or 2 $C_1$-$C_3$ alkyl, 1 or 2 $C_2$-$C_3$ alkoxy, 1 or 2 $C_1$-$C_3$ alkyl amine or 1 or 2 $C_2$-$C_3$ alkoxy amine.

2. The method according to claim 1, wherein R2 represents H or a 5 or 6 membered heteroaromatic ring with 1 or 2 N, which heteroaromatic ring is optionally substituted with 1 or 2 $C_1$-$C_3$ alkyl, 1 or 2 $C_1$-$C_3$ alkoxy, 1 or 2 $C_1$-$C_3$ alkylamine or 1 or 2 $C_1$-$C_3$ alkoxy amine.

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Peptide Substrate of LRRK2 Kinase

<400> SEQUENCE: 1

Gly Ala Gly Arg Leu Gly Arg Asp Lys Tyr Lys Thr Leu Arg Gln Ile
1               5                   10                  15

Arg Gln

3. The method according to claim 1, wherein R2 represents a heteroaromatic ring selected from the group consisting of:

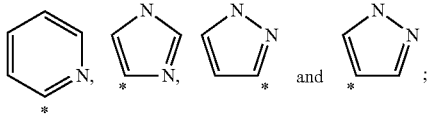

optionally substituted with 1 or 2 groups each independently selected from the group consisting of $CF_3$, halogen, $C_1$-$C_3$ alkyl, $C_1$-$C_3$ alkoxy, $C_1$-$C_3$ alkylamine and $C_1$-$C_3$ alkoxy amine, wherein * denotes the attachment point.

4. The method according to claim 1, wherein R3 represents an aromatic ring selected from the group consisting of:

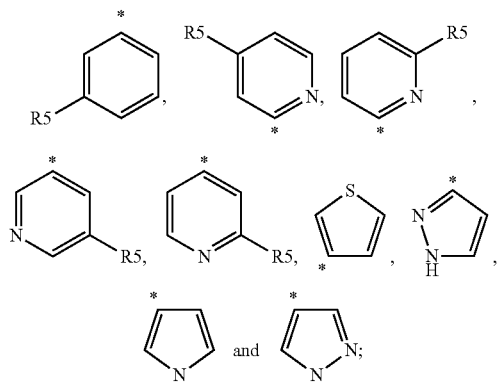

wherein R5 represent H, $C_1$-$C_3$ alkyl or $C_1$-$C_3$ alkoxy, and * denotes the attachment point.

5. The method according to claim 1, wherein R3-L-R4 are selected from the group consisting of:

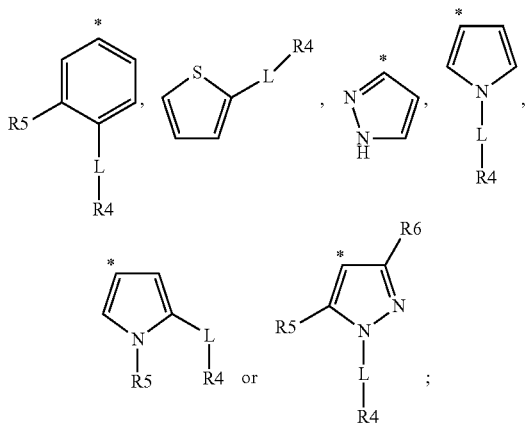

wherein R5 and R6 each independently represent H, $C_1$-$C_3$ alkyl or $C_1$-$C_3$ alkoxy, and * denotes the attachment point.

6. The method according to claim 1, wherein R4 represents

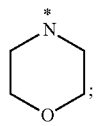

wherein * denotes the attachment point.

7. The method according to claim 1, wherein said compound according to Formula A is selected from the group consisting of:
(1) 4-(3-Methoxyphenyl)-1H-pyrrolo[2,3-b]pyridine-3-carbonitrile;
(2) 4-(3-Methylphenyl)-1H-pyrrolo[2,3-b]pyridine-3-carbonitrile;
(3) 4-(3-Ethylphenyl)-1H-pyrrolo[2,3-b]pyridine-3-carbonitrile;
(4) 4-(Thiophen-3-yl)-1H-pyrrolo[2,3-b]pyridine-3-carbonitrile;
(5) 4-[4-(Morpholin-4-ylmethyl)phenyl]-1H-pyrrolo[2,3-b]pyridine-3-carbonitrile;
(6) 4-[1-(Morpholin-4-ylmethyl)pyrrol-3-yl]-1H-pyrrolo[2,3-b]pyridine-3-carbonitrile;
(7) 4-[3-Methyl-4-(morpholin-4-ylmethyl)phenyl]-1H-pyrrolo[2,3-b]pyridine-3-carbonitrile;
(8) 4-{4-[(Dimethylamino)methyl]-3-methylphenyl}-1H-pyrrolo[2,3-b]pyridine-3-carbonitrile;
(9) 4-[3-Ethyl-4-(morpholin-4-ylmethyl)phenyl]-1H-pyrrolo[2,3-b]pyridine-3-carbonitrile;
(10) 4-[3-Methoxy-4-(morpholin-4-ylmethyl)phenyl]-1H-pyrrolo[2,3-b]pyridine-3-carbonitrile;
(11) 6-Amino-4-phenyl-1H-pyrrolo[2,3-b]pyridine-3-carbonitrile;
(12) 6-Amino-4-(3-methylphenyl)-1H-pyrrolo[2,3-b]pyridine-3-carbonitrile,
(13) 6-[(1-Methylpyrazol-3-yl)amino]-4-phenyl-1H-pyrrolo[2,3-b]pyridine-3-carbonitrile;
(14) 4-(3-Methylphenyl)-6-[(1-methylpyrazol-3-yl)amino]-1H-pyrrolo[2,3-b]pyridine-3-carbonitrile;
(15) 4-[3-Methyl-4-(morpholin-4-yl methyl)phenyl]-6-[(1-methylpyrazol-3-yl)amino]-1H-pyrrolo[2,3-b]pyridine-3-carbonitrile;
(16) 6-[(1-Methylpyrazol-4-yl)amino]-4-phenyl-1H-pyrrolo[2,3-b]pyridine-3-carbonitrile;
(17) 4-Phenyl-6-(pyridin-2-ylamino)-1H-pyrrolo[2,3-b]pyridine-3-carbonitrile;
(18) 6-{[1-Methyl-4-(trifluoromethyl)-1H-pyrazol-3-yl]amino}-4-(5-methylpyridin-3-yl)-1H-pyrrolo[2,3-b]pyridine-3-carbonitrile;
(19) 6-[(4-Chloro-1-methyl-1H-pyrazol-3-yl)amino]-4-(4-methylpyridin-2-yl)-1H-pyrrolo[2,3-b]pyridine-3-carbonitrile;
(20) 6-[(1,4-Dimethyl-1H-pyrazol-3-yl)amino]-4-(6-methylpyridin-2-yl)-1H-pyrrolo[2,3-b]pyridine-3-carbonitrile;
(21) 6-{[1-Methyl-4-(trifluoromethyl)-1H-pyrazol-3-yl]amino}-4-(6-methylpyridin-2-yl)-1H-pyrrolo[2,3-b]pyridine-3-carbonitrile;
(22) 6-[(1-Methyl-1H-pyrazol-3-yl)amino]-4-(5-methylpyridin-3-yl)-1H-pyrrolo[2,3-b]pyridine-3-carbonitrile; and
(23) 6-[(1,4-Dimethyl-1H-pyrazol-3-yl)amino]-4-(2-methylpyridin-4-yl)-1H-pyrrolo[2,3-b]pyridine-3-carbonitrile.

8. A method for the treatment of Lewy body dementia or Parkinson's disease comprising the administration of a therapeutically effective amount of a pharmaceutical composition comprising a compound according to Formula A, or a pharmaceutically acceptable salt of said compound, to a subject in need thereof, wherein said compound according to Formula A is:

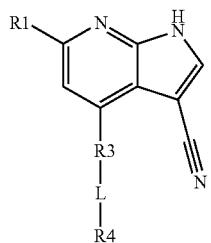

Formula A wherein
R1 represents a NHR2 group;
R2 represents a heteroaromatic ring selected from the group consisting of:

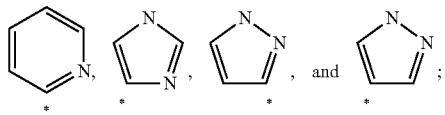

optionally substituted with 1 or 2 groups each independently selected from the group consisting of $CF_3$, halogen, $C_1$-$C_3$ alkyl, $C_1$-$C_3$ alkoxy, $C_1$-$C_3$ alkylamine and $C_1$-$C_3$ alkoxy amine, wherein * denotes the attachment point;
R3 represents a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 $C_1$-$C_3$ alkyl, 1 or 2 $C_1$-$C_3$ alkoxy or a trifluoromethyl;
L is absent or represents $(CH_2)_n$, wherein n=1 or 2; and
R4 represents H, $NH_2$ or a 5 or 6 membered heterocyclic ring with 1 or 2 heteroatom(s) selected from N or O, which heterocyclic ring is optionally substituted with 1 or 2 $C_1$-$C_3$ alkyl, 1 or 2 $C_2$-$C_3$ alkoxy, 1 or 2 $C_1$-$C_3$ alkyl amine or 1 or 2 $C_2$-$C_3$ alkoxy amine.

9. A method for the treatment of Lewy body dementia or Parkinson's disease comprising the administration of a therapeutically effective amount of a pharmaceutical composition comprising a compound according to Formula A, or a pharmaceutically acceptable salt of said compound, to a subject in need thereof, wherein said compound according to Formula A is:

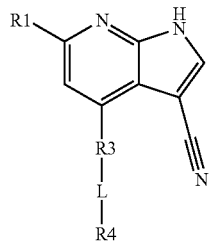

Formula A wherein
R1 represents a NHR2 group;
R2 represents H or a 5 or 6 membered heteroaromatic ring with 1 or 2 N, which heteroaromatic ring is optionally substituted with 1 or 2 groups each independently selected from the group consisting of: $CF_3$, halogen, $C_1$-$C_3$ alkyl, $C_1$-$C_3$ alkoxy, $C_1$-$C_3$ alkylamine and $C_1$-$C_3$ alkoxy amine;
R3 represents a 5 or 6 membered aromatic ring or a 5 or 6 membered heteroaromatic ring with 1 or 2 heteroatoms(s) selected from S or N, which aromatic ring or heteroaromatic ring is optionally substituted with H, OH, 1 or 2 $C_1$-$C_3$ alkyl, 1 or 2 $C_1$-$C_3$ alkoxy or a trifluoromethyl;
L is absent or represents $(CH_2)_n$, wherein n=1 or 2; and
R4 represents

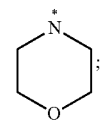

wherein * denotes the attachment point.

10. The method according to claim 1, wherein said Lewy body dementia or Parkinson's disease is characterised by over-expression of LRRK2 or by a mutated form of LRRK2.

11. The method according to claim 1, wherein said Lewy body dementia or Parkinson's disease is characterised by expression of a mutated form of LRRK2 selected from the group consisting of LRKK2 mutations: G2019S, I2020T, M1646T, G2385R, A419V, N551K, R1398H, K1423K, R1441G, R1441H, R1441C, R1628P, S1647T, Y1699C, I2020T and Y2189C.

12. The method according to claim 1, wherein said method is a method for the treatment of a Parkinson's disease selected from the group consisting of: idiopathic Parkinson's disease, sporadic Parkinson's disease and Parkinson's disease characterised by expression of a G2019S mutated form of LRRK2.

* * * * *